(12) United States Patent
Elischweski et al.

(10) Patent No.: US 6,171,845 B1
(45) Date of Patent: Jan. 9, 2001

(54) **MUTANT *E. COLI* KIZ STRAINS FOR PRODUCTION OF PANTOTHENIC ACID**

(75) Inventors: Frank Elischweski, Leopoldshohe; Jorn Kalinowski, Bielefeld; Alfred Puhler, Bielefeld; Nicole Dusch, Bielefeld; Jurgen Dohmen, Meerbusch; Mike Farwick; Georg Thierbach, both of Bielefeld, all of (DE)

(73) Assignee: Degussa-Huls AG (DE)

( * ) Notice: Under 35 U.S.C. 154(b), the term of this patent shall be extended for 0 days.

(21) Appl. No.: 09/416,756

(22) Filed: Oct. 12, 1999

(30) Foreign Application Priority Data

Oct. 9, 1998  (DE) ............................................. 198 46 499

(51) Int. Cl.⁷ ....................................................... C12N 1/21
(52) U.S. Cl. ....................................................... 435/252.33
(58) Field of Search .................................. 435/41, 252.3, 435/252.33, 476, 243; 536/23.1, 23.2

*Primary Examiner*—Terry Mckelvey
*Assistant Examiner*—Gerald G. Leffers, Jr.
(74) *Attorney, Agent, or Firm*—Pillsbury Madison & Sutro LLP

(57) ABSTRACT

The invention relates to a process for the preparation and improvement of D-pantothenic acid-producing microorganisms by amplification of nucleotide sequences which code for ketopantoate reductase, in particular the panE gene, individually or in combination with one another, and optionally additionally of the ilvC gene, the microorganisms containing these nucleotide sequences, and a process for the preparation of D-pantothenic acid comprising fermentation of these microorganisms, concentration of pantothenic acid in the medium or in the cells of the microorganisms, and isolation of the D-pantothenic acid.

2 Claims, 9 Drawing Sheets

FIG. I

SEQUENCE LISTING

```
<160> NUMBER OF SEQ ID NOS: 18

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence:PCR primer

<400> SEQUENCE: 1
agaagcacaa catcacgagg                                                 20

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence:PCR primer

<400> SEQUENCE: 2
ctccaggaga aggcttgagt                                                 20

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence:PCR primer

<400> SEQUENCE: 3
aggaggacaa tgaaaattac                                                 20

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence:PCR primer

<400> SEQUENCE: 4
tcagtctctt cactaccagg                                                 20

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence:PCR primer

<400> SEQUENCE: 5
aggatacgtt atgaaaccga                                                 20
```

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence:PCR primer

<400> SEQUENCE: 6
acaacgtgac tccttaatgg                                                    20

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence:PCR primer

<400> SEQUENCE: 7
aggagtcacg ttgtgttaat                                                    20

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence:PCR primer

<400> SEQUENCE: 8
aagtattacg ccagctcgac                                                    20

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence:PCR primer

<400> SEQUENCE: 9
aggtagaagt tatgattcgc                                                    20

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence:PCR primer

<400> SEQUENCE: 10
taacaatcaa gcaacctgta                                                    20

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence:PCR primer

<400> SEQUENCE: 11
tgctctctct caacgccgaa                                                    20

<210> SEQ ID NO 12
<211> LENGTH: 20
<212> TYPE: DNA
<213> ORGANISM: Artificial Sequence
<220> FEATURE:

<223> OTHER INFORMATION: Description of Artificial Sequence:PCR primer

<400> SEQUENCE: 12
gaagccgcca accaggataa                                              20

<210> SEQ ID NO 13
<211> LENGTH: 62
<212> TYPE: DNA
<213> ORGANISM: Artificial Sequence
<220> FEATURE:
<223> OTHER INFORMATION: Description of Artificial Sequence:PCR primer

<400> SEQUENCE: 13
gcgcgaattc agatccgcgg ccgcaaagag gagaaattaa ctatgactgc accacacaga   60
ag                                                                 62

<210> SEQ ID NO 14
<211> LENGTH: 36
<212> TYPE: DNA
<213> ORGANISM: Artificial Sequence
<220> FEATURE:
<223> OTHER INFORMATION: Description of Artificial Sequence:PCR primer

<400> SEQUENCE: 14
cgcgactagt ctgcagtcag tcctttctcc agtcac                            36

<210> SEQ ID NO 15
<211> LENGTH: 16
<212> TYPE: DNA
<213> ORGANISM: Artificial Sequence
<220> FEATURE:
<223> OTHER INFORMATION: Description of Artificial Sequence:PCR primer

<400> SEQUENCE: 15
gaagtcatcg aaatag                                                  16

<210> SEQ ID NO 16
<211> LENGTH: 17
<212> TYPE: DNA
<213> ORGANISM: Artificial Sequence
<220> FEATURE:
<223> OTHER INFORMATION: Description of Artificial Sequence:PCR primer

<400> SEQUENCE: 16
tcgtttctgt cttttc                                                  17

<210> SEQ ID NO 17
<211> LENGTH: 41
<212> TYPE: DNA
<213> ORGANISM: Artificial Sequence
<220> FEATURE:
<223> OTHER INFORMATION: Description of Artificial Sequence:Portion of
      plasmid pJD-YHR063c

<400> SEQUENCE: 17
gaattcagat ccgcggccgc aaagaggaga aattaactat g                      41

<210> SEQ ID NO 18
<211> LENGTH: 12
<212> TYPE: DNA
<213> ORGANISM: Artificial Sequence
<220> FEATURE:

-continued

```
<223> OTHER INFORMATION: Description of Artificial Sequence:Portion of
      plasmid pJD-YHR063c

<400> SEQUENCE: 18
ctgcagacta ga                                                         12
```

MUTANT E. COLI KIZ STRAINS FOR PRODUCTION OF PANTOTHENIC ACID

This application is related priority to German Application DE 198 46 499.1, filed Oct. 9, 1998, which disclosure is incorporated herein by reference.

FIELD OF THE INVENTION

Pantothenic acid is a vitamin of commercial importance which is used in cosmetics, medicine, human nutrition and animal nutrition.

BACKGROUND OF THE INVENTION

Pantothenic acid can be prepared by chemical synthesis, or biotechnologically by the fermentation of suitable microorganisms in suitable nutrient solutions. In the chemical synthesis, DL-pantolactone is an important compound. It is prepared in a multi-stage process from formaldehyde, isobutyraldehyde and cyanide. In further process steps, the racemic mixture is separated, D-pantolactone is subjected to a condensation reaction with β-alanine, and D-pantothenic acid is obtained.

An advantage of the fermentative preparation by microorganisms is the direct formation of the desired stereoisomeric D-form.

Various types of bacteria, such as, for example, *Escherichia coli, Arthrobacter ureafaciens, Corynebacterium erythrogenes, Brevibacterium ammoniagenes*, and also yeasts, such as, for example, *Debaromyces castellii*, can produce D-pantothenic acid in a nutrient solution which comprises glucose, DL-pantoic acid and β-alanine, as shown in EPA 0 493 060. EPA 0 493 060 furthermore shows that in the case of *Escherichia coli*, the formation of D-pantothenic acid is improved by amplification of pantothenic acid biosynthesis genes contained on the plasmids pFV3 and pFV5, in a nutrient solution comprising glucose, DL-pantoic acid and β-alanine.

EPA 0 590 857 and U.S. Pat. No. 5,518,906 describe mutants derived from the *Escherichia constrain* IFO3547, such as FV5714, FV525, FV814, FV521, FV221, FV6051 and FV5069, which carry resistances to various antimetabolites, such as salicylic acid, α-ketobutyric acid, β-hydroxyaspartic acid, O-methylthreonine and α-ketoisovaleric acid and produce pantoic acid in a nutrient solution comprising glucose, and D-pantothenic acid in a nutrient solution comprising glucose and β-alanine. It is furthermore shown in EPA 0 590 857 and U.S. Pat. No. 5,518,906 that after amplification of the pantothenic acid biosynthesis genes contained on the plasmid pFV31 in the abovementioned strains, the production of D-pantoic acid in a nutrient solution comprising glucose and the production of D-pantothenic acid in a nutrient solution comprising glucose and β-alanine is improved.

In addition, WO 97/10340 shows that in strains of *Escherichia coli* which form pantothenic acid, pantothenic acid production can be increased further by increasing the activity of the enzyme acetohydroxy acid synthase II, an enzyme of valine biosynthesis.

SUMMARY OF THE INVENTION

It is an object of the present invention to provide an improved process for the preparation of pantothenic acid.

The vitamin pantothenic acid is a product of commercial importance which is used in cosmetics, medicine, human nutrition and animal nutrition. There is therefore a general interest in providing improved processes for the preparation of pantothenic acid. When D-pantothenic acid or pantothenic acid or pantothenate are mentioned in the present application, they are intended to include not only the free acid but also the salts of D-pantothenic acid, such as, for example, the calcium, sodium, ammonium or potassium salt.

The invention provides a process for the preparation and improvement of pantothenic acid-producing microorganisms by amplification, in particular over-expression, of nucleotide sequences which code for ketopantoate reductase, in particular sequences of the panE gene, individually or in combination with one another, and optionally, in addition, sequences of the ilvC gene.

The term "amplification" in this connection is intended to mean an increase in the intracellular activity of one or more enzymes which are coded by the corresponding DNA by increasing the number of copies of the gene(s), using a potent promoter or a gene which codes for a corresponding enzyme having a high specific activity, and optionally combining these measures.

In particular, it has been found that over-expression of the panE gene together with the genes panB, panC and panD, further improves the formation of pantothenic acid. To achieve the over-expression, the number of copies of the corresponding genes can be increased by means of plasmid vectors, such as, for example, pBR322 (Sutcliffe, COLD SPRING HARBOR SYMPOSIA ON QUANTITATIVE BIOLOGY 1979, 43: 77–90) or pUC19 (Viera, Gene 1982 19:259–268), or the promoter and regulation region upstream of the structural gene can be mutated. A known example of this is the lac-UV5 mutation of the lac promoter (Winnacker: Gene und Klone, Eine Einführung in die Gentechnologie [From Genes to Clones, Introduction to Gene Technology (Verlag Chemie, Weinheim, Germany, 1990). Expression cassettes which are incorporated upstream of the structural gene act in the same way. This method has been used, for example, by LaVallie et al. (BIO/TECHNOLOGY 11, 187–193 (1993) and in PCT/US97/13359. Alternatively, over-expression of the genes in question can be achieved by changing the composition of the media and the culture procedure. An example of this is the universally known regulation of the expression of the lac operon by glucose and lactose. The present inventors moreover have found that over-expression of the panE gene has an advantageous effect in strains which have resistance mutations to metabolites and antimetabolites, such as, for example, resistance to L-valine. It has furthermore been found that over-expression of the panE gene has an advantageous effect in strains which have defect mutations in genes of metabolic routes, such as, for example, the avtA or ilvE gene, which convert precursors of pantothenic acid or reduce the formation of pantothenic acid.

The microorganisms to which the present invention relates can synthesize pantothenic acid from glucose, sucrose, lactose, fructose, maltose, molasses, starch, cellulose or from glycerol and ethanol. These are fungi, yeasts or, in particular, Gram-positive bacteria, for example, of the genus Corynebacterium, or Gram-negative bacteria, such as, for example, those of the Enterobacteriaceae. Of the family of the Enterobacteriaceae, the genus Escherichia with the species *Escherichia coli* may be mentioned in particular. Within the species *Escherichia coli* there may be mentioned the so-called K-12 strains, such as, for example, the strains MG1655 or W3110 (Neidhard et al.: *Escherichia coli* and Salmonella. Cellular and Molecular Biology (ASM Press, Washington D.C.)) or the *Escherichia coli* wild type strain IFO3547 (Institute of Fermentation, Osaka, Japan) and mutants derived from these. Of the genus Corynebacterium, the species *Corynebacterium glutamicum*, which is known among specialists for its ability to form amino acids, is of particular interest. This species includes wild type strains, such as, for example, *Corynebacterium glutamicum* ATCC13032, *Brevibacterium flavum* ATCC14067, *Corynebacterium melassecola* ATCC17965 and others.

To isolate the ilvC gene and the panE gene, a mutant of, for example, *Escherichia coli* which carries a mutation in the ilvC gene and panE gene, is first prepared.

The nucleotide sequence of the ilvC gene of *Escherichia coli* is known (Wek and Hatfield, Journal of Biological Chemistry 261, 2441–2450 (1986)). Methods for isolation of chromosomal DNA are also known (Sambrook et al.: Molecular Cloning, A Laboratory Manual (Cold Spring Harbor Laboratory Press, 1989). By choosing suitable primers, the ilvC gene can be amplified with the aid of the polymerase chain reaction (Innis et al., PCR protocols. A guide to methods and applications, 1990, Academic Press). It is then introduced into a plasmid vector. Possible plasmid vectors are those which can replicate in the corresponding microorganisms. For *Escherichia coli*, for example, the vectors pSC101 (Vocke and Bastia, Proceedings of the National Academy of Science U.S.A. 80 (21), 6557–6561 (1983)) or pKK223-3 (Brosius and Holy, Proceedings of the National Academy of Science USA 81, 6929 (1984)), for *Corynebacterium glutamicum*, for example, the vector pJC1 (Cremer et al., Mol. Gen. Genet. 220:478–480 (1990)) or pEKEx2 (Eikmanns et al., Gene 102:93–98 (1991)) or pZ8-1 (European Patent Specification 0 375 889) and for *Saccharomyces cerevisiae*, for example, the vector pBB116 (Berse, Gene 25: 109–117 (1983)) or pDG1 (Buxton et al., Gene 37: 207–214 (1985)) are possible for the present invention. Methods for incorporation of DNA fragments into plasmid vectors are described by Sambrook et al.: Molecular Cloning, A Laboratory Manual (Cold Spring Harbor Laboratory Press, 1989). Methods for transformation and electroporation are described by Tauch et al. (FEMS Microbiology Letters 123:343–347 (1994)). A example of such a transformed strain is the *Escherichia coli* strain MG1655/pFE32. Plasmid pFE32 contains the ilvC gene of MG1655 which has been incorporated into the vector pBR322. Another example of such a transformed strain is the *Corynebacterium glutamicum* strain ATCC13032/pFE91. Plasmid pFE91 contains the ilvC gene of ATCC13032 which has been incorporated into the vector pECm3. Plasmid pECm3 is a derivative of plasmid pECm2 (Tauch, 1994, FEMS Microbiological Letters, 123:343–348), the kanamycin resistance gene of which has been removed by a BglII and BamHI restriction with subsequent re-ligation For incorporation of a mutation into the ilvC gene which eliminates its function, for example, a deletion or insertion can be used. To generate a deletion, an internal part of the nucleotide sequence of the structural gene can be removed with the aid of suitable restriction enzymes and subsequent linking of the ends formed. The ilvC gene mutated in this manner has no function. A second gene which codes for a resistance to an antibiotic can be incorporated into the ilvC gene in the same manner. The ilvC gene mutated in this manner also has no function. The ilvC gene mutated in this manner can then be introduced into a microorganism to replace the wild type gene in the chromosome thereof. Methods of how to carry out this gene exchange are known in the literature. For *Escherichia coli*, the method described by Hamilton et al. (Journal of Bacteriology 171, 4617–4622 (1989)), which is based on temperature-sensitive replication mutants of the plasmid pSC101, can be employed.

pMAK705 is an example of such a plasmid. For *Corynebacterium glutamicum*, the method of gene exchange described by Schwarzer and Pühler (BIO/TECHNOLOGY 9, 84–87 (1991)), in which non-replicative plasmid vectors are used, can be used. For *Saccharomyces cerevisiae* a method of controlled gene exchange is described by Roca et al. (Nucleic Acid Research 20(17), 4671–4672 (1992)).

A mutated ilvC gene can be prepared, for example, from a wild type ilvC gene as follows. Plasmid pFE32 comprised of pBR322, is incorporated into the BamHI restriction cleavage site of the ilvC wild type gene. The aacC1 gene, which codes for resistance to the antibiotic gentamycin, was incorporated into the KpnI cleavage site of the ilvC gene of pFE32 (Schweizer, BioTechniques 15 (5), 831–834 (1993)). The plasmid pFE33 obtained in this manner contains the ilvC::aacC1 allele, which can no longer form functional ilvC gene product. The ilvC::aacC1 allele was removed from the plasmid pFE33 and introduced into the SphI cleavage site of the plasmid pMAK705, as a result of which the plasmid pDB1 was formed. Plasmid pDB1 is a plasmid vector which is capable of allele exchange and comprises on the one hand pMAK705 and on the other hand the ilvC::aacC1 allele. Plasmid pDB1 was used in the method described by Hamilton et al. to exchange the wild type ilvC gene present in MG1655 for the ilvC::aacC1 allele. The strain formed in this manner is designated FE4.

To isolate a mutant of FE4 which carries a mutation in the panE gene, the strain FE4 was subjected to a transposon mutagenesis with the transposon Tn5. Transposon Tn5 is described by Auerswaid (COLD SPRING HARBOR SYMPOSIA ON QUANTITATIVE BIOLOGY 45, 107–113 (1981)). The method of transposon mutagenesis is described, for example, in the handbook by Miller, A: Short Course in Bacterial Genetics, A Laboratory Manual and Handbook for *Escherichia coli* and Related Bacteria (Cold Spring Harbor Laboratory Press, 1992). The method is furthermore described by Simon (Gene 80, 161–169 (1998)) and also in the handbook by Hagemann: Gentechnologische Arbeitsmethoden [Working Methods of Genetic Engineering] (Gustav Fischer Verlag, 1990) and in numerous other publications accessible to the public. Mutants can also be produced after mutagenesis with ultraviolet light or after treatment with a mutation-inducing chemical, such as, for example, N-methyl-N'-nitro-N-nitrosoguanidine. Among the mutants obtained in this manner, after testing the growth substance requirements, in particular the pantothenic acid requirement, those mutants which carry a mutation in a gene of pantothenic acid biosynthesis can be isolated. Those mutants in need of pantothenic acid which can utilize not ketopantoate but pantoate as a growth substance and are therefore mutated in the panE gene which codes for ketopantoate reductase (EC 1.1.1169) are of particular interest. An example of this is the strain FE5 obtained in this manner, which, in addition to the ilvC::aacC1 mutation, carries a panE::Tn5 mutation.

Microorganisms which carry a defect mutation in the ilvC and panE gene, such as, for example, the *Escherichia coli* strain FE5, can be used as cloning hosts for isolation of the ilvC gene and of the particularly interesting panE gene, or of nucleotide sequences which code for proteins with ketopantoate reductase activity.

A gene library of the microorganisms of interest was created in this context. The construction of gene libraries is described in generally known textbooks and handbooks. The textbook by Winnacker: Gene und Klone, Eine Einführung in die Gentechnologie [From Genes to Clones, Introduction to Gene Technology] (Verlag Chemie, Weinheim, Germany, 1990) or the handbook by Sambrook et al.: Molecular Cloning, A Laboratory Manual (Cold Spring Harbor Laboratory Press, 1989) may be mentioned, for example. A known gene library is that of the *E. coli* K-12 strain W3110 described by Kohara et al. (Cell 50, 495–508 (1987)). It has since become possible to acquire gene libraries of various microorganisms commercially, such as, for example, a gene library of *Saccharomyces pombe* strain Sp63 from Stratagene (Heidelberg, Germany) in the plasmid lambda FIX II (Elgin, Strategies 4: 6–7(1991)), a gene library of the *Escherichia coli* strain W1485 from CLONTECH (Heidelberg, Germany) in the plasmid pGAD10 (Kitts, CLONTECH (Heidelberg, Germany) Vectors On Disc version 1.3, 1994), the nucleotide sequence of which is accessible under the GenBank accession number U13188. The gene library prepared in the manner described above can then be introduced by transformation into the host FE5 described above. By way of example, the pGAD10 gene library of W1485 was thus introduced into the strain FE5 by transformation, and the resulting transformants were investigated for their ability to grow on a pantothenic acid-free nutrient medium. The insertions contained in the plasmid DNA of the resulting pantothenic acid-prototrophic transformants can be investigated by determination of the nucleotide sequence. Methods for determination of nucleotide sequences can be found, for example, in Sanger et al. (Proceedings of the National Academy of Science USA 74:5463–5467 (1977)). Nucleotide sequences can be assigned to genes by means of homology investigations. One possibility for this homology search is comparison with nucleotide sequences of the EMBL and GenBank databanks, which can be carried out by means of the BLAST E-mail Service (Altschul, Journal of Molecular Biology 215, 403–410 (1990)). An example of such a transformant is the *Escherichia coli* strain FE5/pFEbank16 which carries the panE gene of the *E. coli* strain MG1655.

The panE gene isolated and identified in the manner described can then be expressed in a desired microorganism. For this purpose, it is amplified by plasmid vectors. These in turn can be equipped with signal structures, which ensure efficient transcription and translation. An overview of expression vectors is to be found, for example, in the textbook by Winnacker: Gene und Klone, Eine Einführung in die Gentechnologie [From Genes to Clones, Introduction to Gene Technology] (Verlag Chemie, Weinheim, Germany, 1990) or in Sambrook et al.: Molecular Cloning, A Laboratory Manual (Cold Spring Harbor Laboratory Press, 1989). Expression signals, such as, for example, the tac promoter, can furthermore be incorporated into the chromosome upstream of the panE gene. Such methods are described in WO 98/04715. The panE gene to be expressed can be removed from the cloned chromosomal DNA fragment, or it can be amplified in turn with the aid of the polymerase chain reaction. The amount of ketopantoate reductase present in the microorganism in question can be determined with the aid of the method described by Shimizu et al. (Journal of Biological Chemistry 263: 12077–12084 (1988)). A example of such a strain is the *Escherichia coli* strain MG1655/pFE65. Plasmid pFE65, comprising the vector pKK223-3, has been incorporated into the EcoRI restriction cleavage site of the panE gene of *Escherichia coli* MG1655.

According to the invention, it has proved advantageous to amplify, in particular to over-express, one or more genes of pantothenic acid biosynthesis in addition to the panE gene, which codes for ketopantoate reductase. These include the genes which code for the enzymes ketopantoate hydroxymethyltransferase (EC 4.1.2.12), aspartate 1-decarboxylase (EC 4.1.1.11) and pantothenate synthetase (EC 6.3.2.1). In *Escherichia coli*, these genes are designated panB, panD and panC (Miller, A Short Course in Bacterial Genetics, A Laboratory Manual and Handbook for *Escherichia coli* and Related Bacteria (Cold Spring Harbor Laboratory Press, 1992)). For this, the genes can be incorporated into various compatible plasmid vectors. Examples of these are described by Bartolome et al. (Gene 102, 75–78 (1991). Gene expression can furthermore be increased by changing the chromosomal signal structures lying upstream. The genes in question can, moreover, be placed under the control of a common promoter, in an arrangement in succession, and incorporated into a plasmid vector and introduced into a suitable microorganism. An example of this is *Escherichia coli* strain MG1655/pFE80. The plasmid pFE80 comprises the plasmid pKK223-3, which contains the genes panB, panD, panC and panE in the stated sequence. The tac promoter is contained in pFE80 as an expression signal upstream of the panB gene.

It has also proved advantageous to over-express the panE gene and the expression unit consisting of the genes panB, panD, panC and panE in host strains which contain chromosomal mutations.

It is possible to use mutations, individually or together, which produce resistances to metabolism products, such as, for example, L-valine or α-ketoisovaleric acid, or to analogues of metabolism products, such as, for example, β-hydroxyaspartic acid or O-methylthreonine. Such mutants occur spontaneously or can be produced by mutagenesis with ultraviolet light or treatment with a mutation-inducing chemical, such as, for example, N-methyl-N'-nitro-N-nitrosoguanidine, and can then be selected on agar plates containing the appropriate substance. Processes for inducing mutation and for selection are generally known and can be found, inter alia, in Miller (A Short Course in Bacterial Genetics, A Laboratory Manual and Handbook for *Escherichia coli* and Related Bacteria (Cold Spring Harbor Laboratory Press, 1992)) or in the handbook "Manual of Methods for General Bacteriology" of the American Society for Bacteriology (Washington D.C., USA). An example of such a mutant is *Escherichia coli* strain FE6, which has been isolated as a spontaneously occurring, L-valine-resistant mutant of the strain MG1655.

Adverse or troublesome chromosomally coded metabolism reactions can furthermore be eliminated in a controlled manner. For this, insertions or deletions are introduced into the corresponding genes and the mutated genes or alleles formed in this manner are incorporated into the chromosome of the host. The methods which have been described above for mutation of the ilvC gene can be employed. An example of such a mutant is the *Escherichia coli* strain FE7, which carries an avtA::aadB mutation in the chromosome. This is the strain MG1655, in which the aadB gene from plasmid pHP45 Ω, which imparts resistance to streptomycin, has been introduced into the avtA gene (Prentki and Krisch, Gene 29, 303–313 (1984)). The panE gene can then be over-expressed in the host strains prepared in this manner, either alone or in combination with other genes. Examples of these are the strains FE6/pFE80 and FE7/pFE80.

The microorganisms prepared according to the invention can be cultured continuously or discontinuously in the batch process or in the fed batch (feed process) or repeated fed batch process (repetitive feed process) for the purpose of pantothenic acid production. A summary of known culture methods is described in the textbook by Chmiel (Bioprozesstechnik 1. Einführung in die Bioverfahrenstechnik [Bioprocess Technology 1. Introduction to Bioprocess Technology (Gustav Fischer Verlag, Stuttgart, 1991)) or in the textbook by Storhas (Bioreaktoren und periphere Einrichtungen [Bioreactors and Peripheral Equipment] (Vieweg Verlag, Braunschweig/Wiesbaden, 1994)). The culture medium to be used must meet the requirements of the particular microorganisms. Descriptions of culture media for various microorganisms are contained in the handbook "Manual of Methods for General Bacteriology" of the American Society for Bacteriology (Washington D.C., USA, 1981). Sugars and carbohydrates, such as, for example, glucose, sucrose, lactose, fructose, maltose, molasses, starch and cellulose, oils and fats, such as, for example, soya oil, sunflower oil, groundnut oil and coconut fat, fatty acids, such as e.g. palmitic acid, stearic acid and linoleic acid, alcohols, such as, for example, glycerol and ethanol, and organic acids, such as, for example, acetic acid, can be used as the source of carbon. These substances can be used individually or as a mixture. Organic nitrogen-containing compounds, such as peptones, yeast extract, meat extract, malt extract, corn steep liquor, soya bean flour and urea, or inorganic compounds, such as ammonium sulphate, ammonium chloride, ammonium phosphate, ammonium carbonate and ammonium nitrate, can be used as the source of nitrogen. The sources of nitrogen can be used individually or as a mixture. Phosphoric acid, potassium dihydrogen phosphate or dipotassium hydrogen phosphate or the corresponding sodium-containing salts can be used as the source of phosphorus. The culture medium must furthermore comprise salts of metals, such as, for example, magnesium sulfate or iron sulfate, which are necessary for growth. Finally, essential growth substances, such as amino acids and vitamins, can be employed in addition to the abovementioned substances. Precursors of pantothenic acid, such as β-alanine or ketopantoic acid and salts thereof, can also be added to the culture medium. The starting substances mentioned can be added to the culture in the form of a single batch, or can be added during the cultivation in a suitable manner.

Basic compounds, such as sodium hydroxide, potassium hydroxide and ammonia, or acid compounds, such as phosphoric acid and sulfuric acid, can be used to control the pH of the culture. Antifoams, such as, for example, fatty acid polyglycol esters or silicone oils, can be employed to control the development of foam. Suitable substances having a selective action, for example, antibiotics, can be added to the medium to maintain the stability of plasmids. To maintain aerobic conditions, oxygen or oxygen-containing gas mixtures, such as, for example, air, are introduced into the culture. The temperature of the culture is usually 20° C. to 50° C., and preferably 25° C. to 45° C. Culturing is continued until a maximum of pantothenic acid has formed. This target is usually reached within 10 hours to 160 hours.

The concentration of pantothenic acid formed can be determined by known processes (Velisek; Chromatographic Science 60, 515–560 (1992)).

The following microorganisms were deposited at the Deutsche Sammlung für Mikrorganismen und Zellkulturen (DSMZ=German Collection of Microorganisms and Cell Cultures, Braunschweig, Germany) on Aug. 18, 1998 in accordance with the Budapest Treaty:

*Escherichia coli* K12 strain FE5 as DSM12378
*Escherichia coli* K12 strain MG1655/pFE32 as DSM12413
*Escherichia coli* K12 strain MG1655/pFE65 as DSM12382
*Escherichia coli* K12 strain MG1655/pFE80 as DSM12414
*Escherichia coli* K12 strain FE6 as DSM12379
*Escherichia coli* K12 strain FE7 as DSM12380

The process according to the invention provides the person skilled in the art with a new tool for improving the formation of pantothenic acid by microorganisms in a controlled manner.

Figure 1:
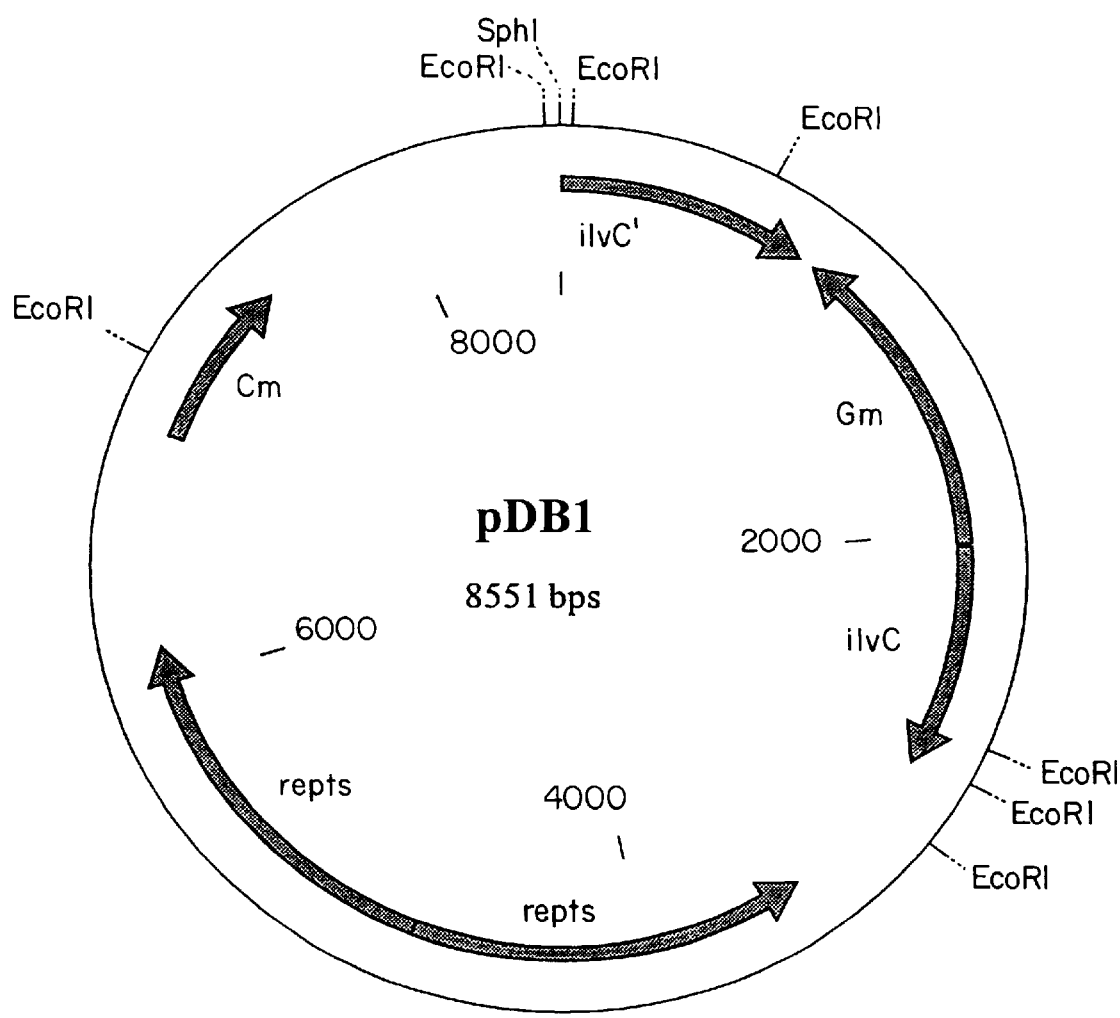
FIG. 1: Map of the plasmid pDB1
Figure 2:
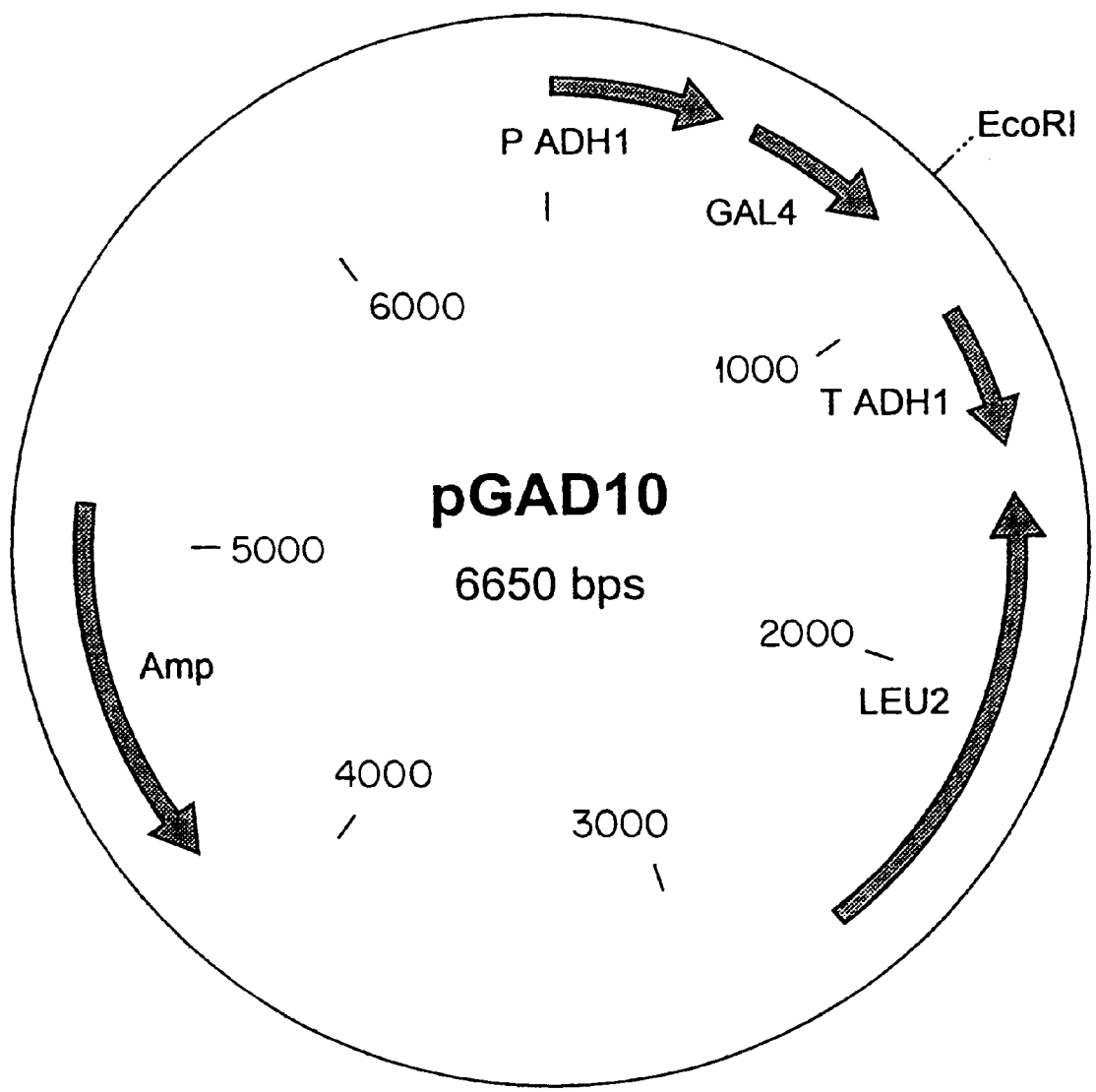
FIG. 2: Map of the plasmid pGAD10
Figure 3:
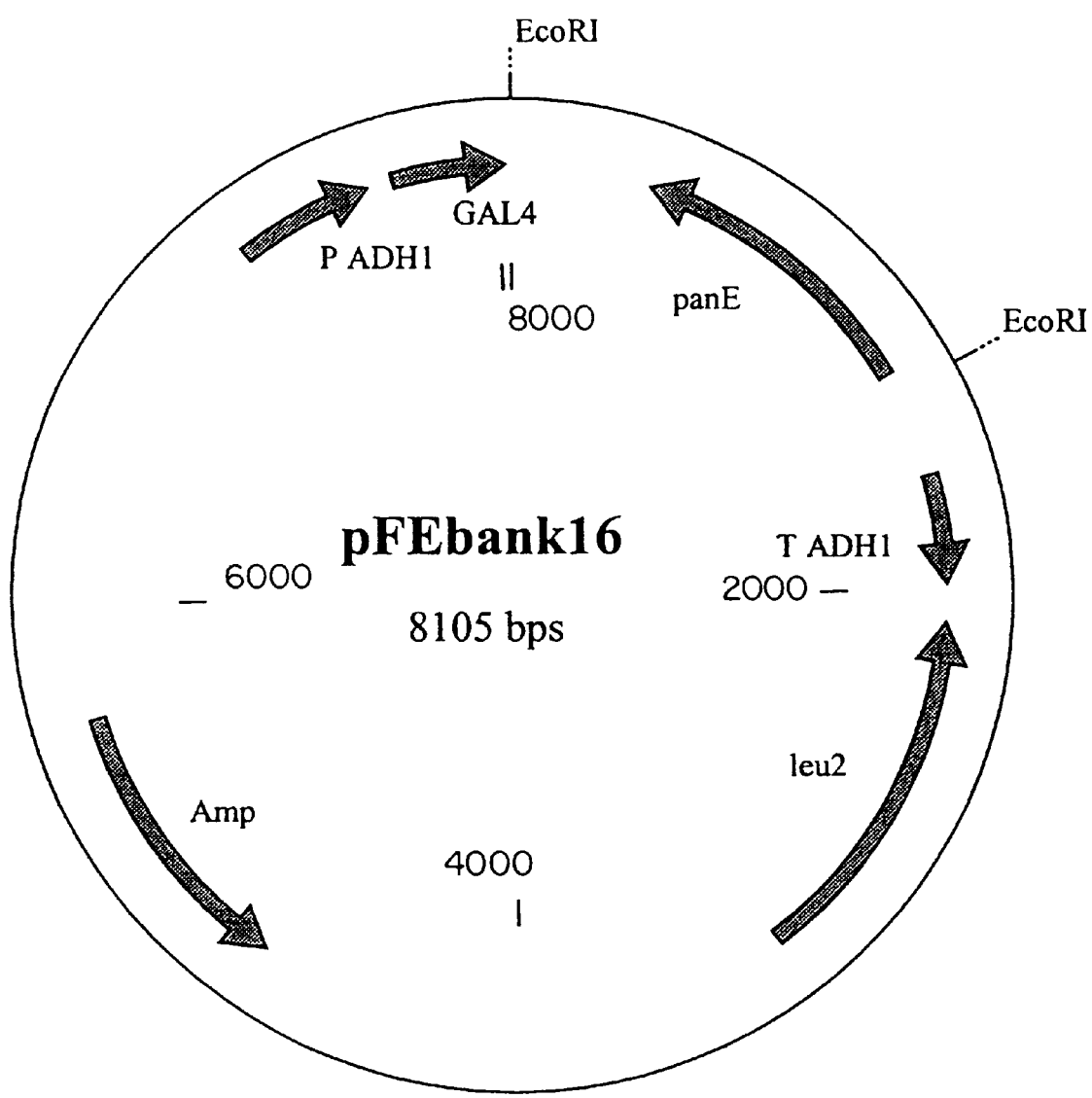
FIG. 3: Map of the plasmid pFEbank 16
Figure 4:
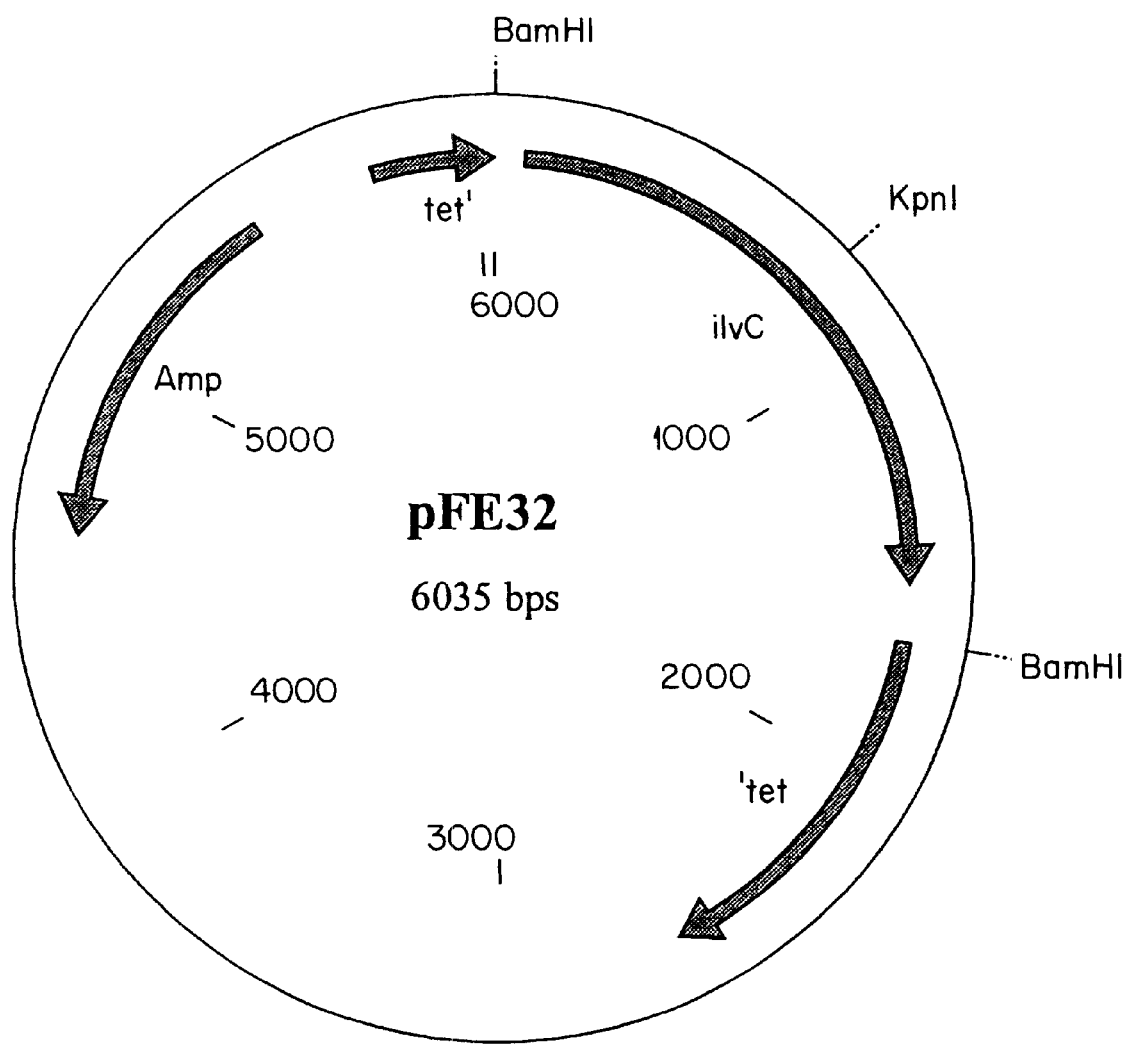
FIG. 4: Map of the plasmid pFE32
Figure 5:
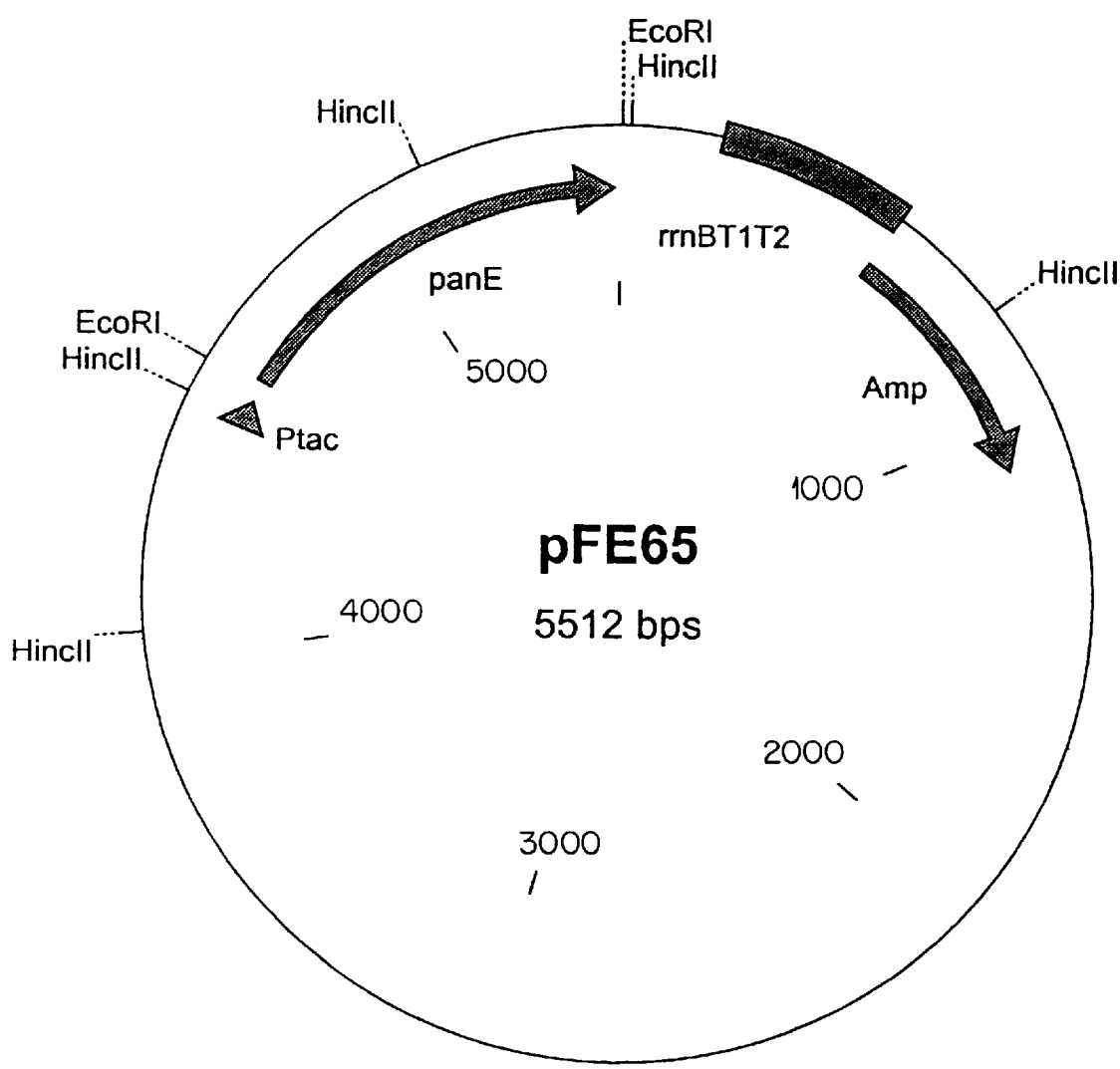
FIG. 5: Map of the plasmid pFE65
Figure 6:
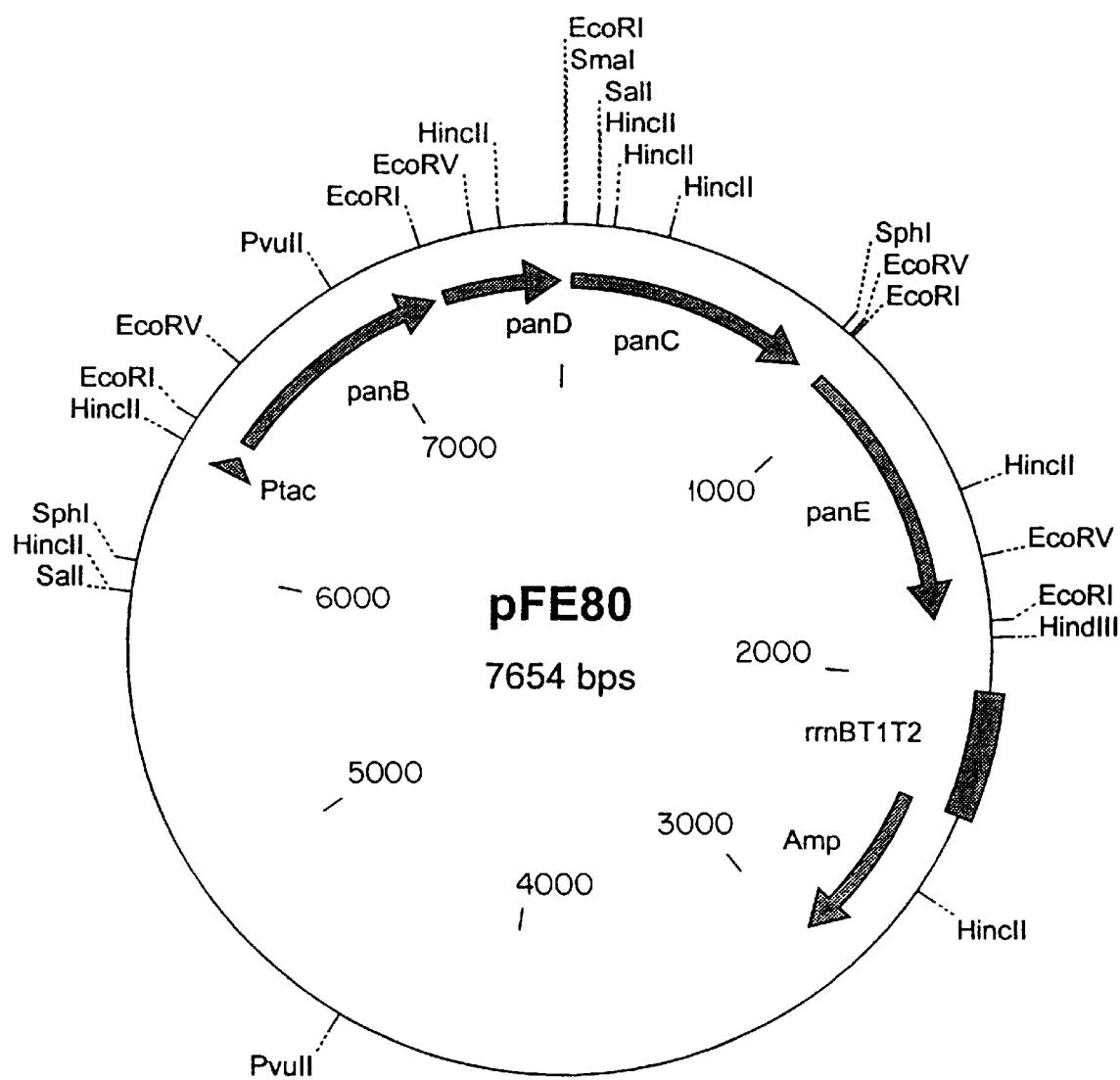
FIG. 6: Map of the plasmid pFE80
Figure 7:
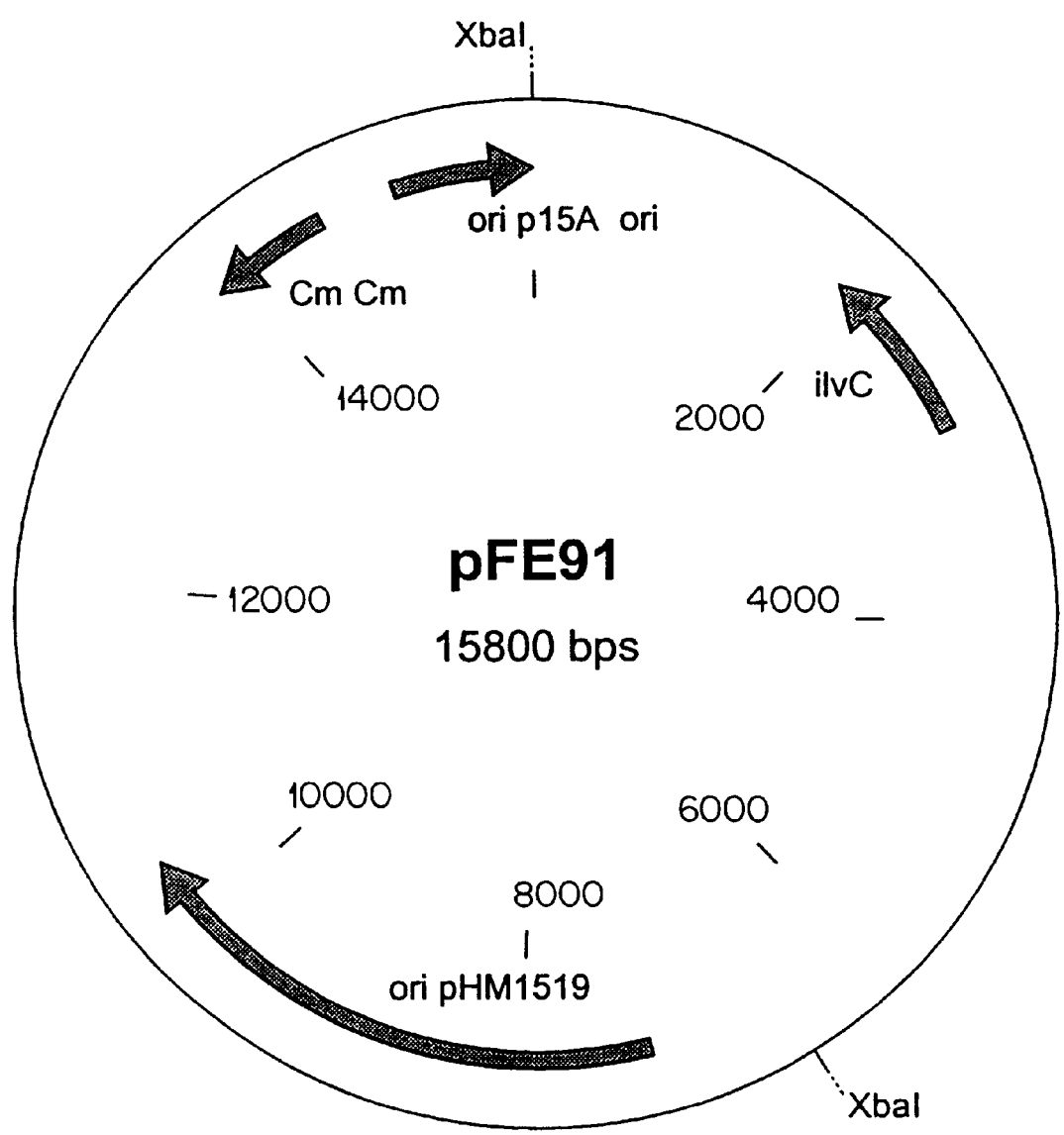
FIG. 7: Map of the plasmid pFE91

The base pair numbers stated are approx. values obtained in the context of reproducibility.

The abbreviations used in the figures have the following meaning:

rrnBT1T2: transcription terminator of the rrnB gene
Ptac: tac promoter
P AHD1: promoter of the ADH1 gene from *Saccharomyces cerevisiae*
T ADH1: terminator of the ADH1 gene from *Saccharomyces cerevisiae*
repts: thermosensitive replication origin
ilvC: coding region of the ilvC gene
ilvO': 5' region of the ilvC gene
'ilvC: 3' region of the ilvC gene
panB: coding region of the panB gene
panC: coding region of the panC gene
panD: coding region of the panD gene
panE: coding region of the panE gene
Amp: resistance gene for ampicillin
tet': 5' region of the tet gene
'tet: 3' region of the tet gene
Cm: resistance gene for chloramphenicol
Gm: resistance gene for gentamicin
Gal4: regulator for galactose-inducible genes from *Saccharomyces cerevisiae*
bps: base pairs
LEU2: beta-isopropyl malate dehydrogenase gene of *Saccharomyces cerevisiae*
2 μ: sequences of the endogenous 2 μ plasmid of *Saccharomyces cerevisiae*
$Ap^R$: beta-lactamase gene
P-CUP1: promoter of the *Saccharomyces cerevisiae* CUP1 gene (metallothionein)
T-CYC1: terminator of the CYC1 gene (cytochrome C) of *Saccharomyces cerevisiae*
ORF: open reading frame
SD: Shine-Dalgarno sequence
EcoRI: cleavage site of the restriction enzyme EcoRI
EcoRV: cleavage site of the restriction enzyme EcoRV
HincII: cleavage site of the restriction enzyme HincII
HindIII: cleavage site of the restriction enzyme HindIII
KpnI: cleavage site of the restriction enzyme KpnI
SalI: cleavage site of the restriction enzyme SalI
SmaI: cleavage site of the restriction enzyme SmaI
SphI: cleavage site of the restriction enzyme SphI
PvuII: cleavage site of the restriction enzyme PvuII
NotI: cleavage site of the restriction enzyme NotI from Norcardia otitidis-cavarium SpeI: cleavage site of the restriction enzyme SpeI from sphaerotilus spec.
XbaI: cleavage site of the restriction enzyme XbaI from Xanthomonas badrii
PstI: cleavage site of the restriction enzyme PstI from Providencia stuartii

DETAILED DESCRIPTION OF THE INVENTION

The present invention is explained in more detail in the following examples.

EXAMPLE 1

Preparation of an ilvC::aacC1 panE::Tn5 Mutant of Escherichia coli K12 Strain MG 1655

1. Preparation of the ilvC::aacC1 mutant

PCR primers were synthesized using the nucleotide sequence for the ilvC gene in E. coli K12 MG1655, (EMBL-GenBank: Accession No. M87049), (MWG Biotech (Ebersberg, Germany)). A DNA fragment approximately 1500 bp in size could be amplified with these primers by the standard PCR method of Innis et al. (PCR protocols. A guide to methods and applications, 1990, Academic Press). The chromosomal E. coli K12 MG1655 DNA employed for the PCR was isolated by means of the NucleoSpin C+T Kit (Macherey-Nagel (Düren, Germany), Product Description NucleoSpin C+T, Cat. no. 740952). The size was determined by separation by gel electrophoresis (30 minutes, 10V/cm) in a 0.8% agarose gel.

PCR primers for the ilvC gene from E. coli:

iIvC1 5'- AGAAGCACAACATCACGAGG -3'  (SEQ ID NO:1)

iIvC2 5'- CTCCAGGAGAAGGCTTGAGT -3'  (SEQ ID NO:2)

The PCR product of the ilvC gene was transformed into the plasmid pCR®2.1 and into the E. coli strain TOP10F' (Invitrogen (Leek, The Netherlands), Product Description Original TA Cloning® Kit, Cat. no. KNM2030-01).

Successful cloning was demonstrated by cleavage of the DNA of the plasmid pCR®2.1 ilvC with the restriction enzymes EagI (Pharmacia Biotech (Freiburg, Germany), Product Description EagI, Code no. 27-0885-01), EcoRI (Pharmacia Biotech (Freiburg, Germany), Product Description EcoRI, Code no. 27-0884-03) and KpnI (Pharmacia Biotech (Freiburg, Germany), Product Description KpnI, Code no. 27-0908-01). For this, the plasmid DNA was isolated by means of the QIAprep Spin Plasmid Kit (QIAGEN (Hilden, Germany), Cat. no. 27106) and, after cleavage, separated in a 0.8% agarose gel (30 minutes, 10V/cm).

To isolate the ilvC gene from the plasmid pCR®2.1ilvC, the plasmid DNA isolated was cleaved with the enzymes HindIII (Pharmacia Biotech (Freiburg, Germany), Product Description HindIII, Code no. 27-0860-01) and XbaI (Pharmacia Biotech (Freiburg, Germany), Product Description XbaI, Code no. 27-0948-01), the cleavage batch was separated in 0.8% agarose gel (30 minutes, 10V/cm) and the 1.5 kbp ilvC fragment was isolated with the aid of the GLASSMAX™ Kit (GIBCO BRL (Eggenstein, Germany), Product Description GLASSMAX™ Spin Cartridges, Cat. no.15590-052). The ilvC fragment isolated was ligated with the plasmid pMAK705, also cleaved with HindIII and XbaI (Hamilton et al., Journal of Bacteriology 1989,171: 4617–4622), by means of T4 DNA ligase (Pharmacia Biotech (Freiburg, Germany), Product Description T4 DNA Ligase, Code no.27-0870-03), and the E. coli strain DH5αmcr (Grant, Proceedings of the National Academy of Science 1990, 87: 4645–4649) was electroporated with the ligation batch (Tauch, FEMS Microbiology Letters 1994, 123: 343–347). Selection for plasmid-carrying cells was made by plating out the electroporation batch on LB agar (Lennox, Virology 1955,1: 190), to which 25 µg/ml chloramphenicol (Sigma (Deisenhofen, Germany) Code no. C 0378) had been added, and incubation at 30° C. for 24 hours. The required plasmid could be identified, after isolation of the DNA and checking of the cleavage, with the enzymes HindIII, XbaI and KpnI in one clone by subsequent gel electrophoresis in 0.8% agarose gel (30 minutes, 10V/cm), and was called pFE30.

To isolate the ilvC gene from the plasmid pFE30, the plasmid DNA isolated was cleaved with the enzyme BamHI (Pharmacia Biotech (Freiburg, Germany), Product Description BamHI, Code no. 27-0868-03), the cleavage batch was separated in 0.8% agarose gel (30 minutes, 10V/cm) and the 1.5 kbp ilvC fragment was isolated with the aid of the GLASSMAX™ Kit. The ilvC fragment isolated was ligated with the plasmid pBR322, also cleaved with BamHI (Sutcliffe, COLD SPRING HARBOR SYMPOSIA ON QUANTITATIVE BIOLOGY 1979, 43: 77–90), by means of T4 DNA Ligase and the E. coli strain DH5αmcr was electroporated with the ligation batch. Selection for plasmid-carrying cells was made by plating out the electroporation batch on LB agar, to which 100 µg/ml ampicillin (Sigma (Deisenhofen, Germany) Code no. A 9518) had been added, and incubation at 37° C. for 24 hours. The colonies obtained were inoculated in parallel on to LB+ampicillin agar and LB+(5 µg/ml)tetracycline (Sigma (Deisenhofen, Germany), Code no. T3383). DNA from tetracycline-sensitive colonies was isolated with the QIAprep Spin Plasmid Kit and successful cloning was verified by means of a BamHI and KpnI cleavage and subsequent separation in 0.8% agarose gel (30 minutes, 10V/cm). The plasmid constructed was called pFE32.

An aacC1 gene was cloned into the KpnI cleavage site of the plasmid pFE32 and the resulting plasmid was called pFE33. For this, the aacC1 gene was isolated from an agarose gel (30 minutes, 10V/cm) in which a KpnI restriction batch of the plasmid pMS255 (Becker, Gene 1995, 162: 37–39) was separated. Ligation was carried out with T4 DNA ligase. After electroporation of the ligation batch into the strain DH5αmcr, the transformants were selected on PA agar (Sambrook, Molecular cloning, $2^{nd}$ edn, Cold Spring Harbor, 1989), to which 10 µg/ml gentamycin (Sigma (Deisenhofen, Germany), Code no. G3632) was added. DNA from gentamycin-resistant colonies was isolated with the QIAprep Spin Plasmid Kit and successful cloning was verified by means of a BamHI and KpnI cleavage and subsequent separation in 0.8% agarose gel (30 minutes, 10V/cm).

The ilvC::aacC1 fragment was cleaved from plasmid pFE33 by means of SphI (Pharmacia Biotech (Freiburg, Germany), Product Description SphI, Code no. 27-0951-01) restriction, separated in 0.8% agarose gel (30 minutes, 10V/cm) and isolated with the GLASSMAX™ Kit. The fragment was ligated with the plasmid pMAK705, which was cleaved with SphI, by means of T4 DNA ligase, the ligation batch was electroporated into the strain DH5αmcr and transformants were selected by incubation on PA+gentamycin agar for 24 hours at 30° C. DNA from gentamycin-resistant colonies was isolated with the QIAprep Spin Plasmid Kit and successful cloning was verified by means of an SphI and EcoRI cleavage in 0.8% agarose gel (30 minutes, 10V/cm). The plasmid constructed was called pDB1.

The chromosomal ilvC gene in the strain E. coliK12 MG1655 was exchanged for the interrupted ilvC::aacC1 fragment with the aid of the plasmid pDB1. A modified method according to Hamilton et al. was used for the gene exchange. Plasmid pDB1 was electroporated into the *E. coli* K12 MG1655 strain, and the transformants were then incubated on LB-chloramphenicol agar at 42° C. for 24 hours for selection for cointegrates. For individualization, the resulting colonies were in turn smeared on to the same medium and incubated at 42° C. for 24 hours. For disintegration of the plasmid, individual colonies were incubated in 5 ml LB liquid medium at 42° C. for 24 hours, and a dilution series of the liquid medium was then plated out on LB-chloramphenicol agar. This dilution series was incubated at 30° C. for 24 hours. For curing of the plasmid, individual colonies obtained from the dilution series were cultured in 3 successive individual colony smears on LB agar at 42° C. for in each case 24 hours. To check the phenotype, the resulting individual colonies were inoculated in parallel on to agar plates with the following media: Medium E (Vogel, Journal of Biological Chemistry 1956, 218: 97–106)+glucose (0.4%), medium E+glucose (0.4%) (Sigma (Deisenhofen, Germany), Code no. G8270)+50 µg/ml isoleucine (Sigma (Deisenhofen, Germany), Code no.17268), medium E+glucose (0.4%)+50 µg ketoisovalerate (ICN (Eschwege, Germany), Code no. 151395), medium E+glucose (0.4%)+50 µg/ml isoleucine+50 µg ketoisovalerate, PA medium+gentamycin and LB medium+chloramphenicol. These media were incubated at 37° C. for 48 hours. Of 150 individual colonies tested, there was one of which the phenotype displayed the exchange of the chromosomal ilvC gene for the ilvC::aacC1 fragment. This strain was called FE4.

2. Preparation of the ilvC::aacC1 panE::Tn5 double mutant

The strain FE4 was cultured in 5 ml LB liquid medium+10 mM $MgSO_4$+0.2% maltose (Sigma (Deisenhofen, Germany), Code no. M5885) (LBMgMaI) at 37° C., to an optical density of 0.5. The optical density was measured with a Pharmacia (Freiburg, Germany) Novaspec II photometer at a wavelength of 660 nm. 2 ml of the bacteria solution were centrifuged for 5 min at 3000rpm (Beckmann Model J2-21 Centrifuge, Rotor JA-17). After the pellet had been taken up in 0.5 ml LBMgMaI liquid medium, 30 µl λ::Tn5(Simon, Gene 1989, 80(1):161–169) lysate, approx. $10^8$ bacteriophages, were added to the suspension. This lysate was isolated from the strain *E. coli* K12 C600 (Appleyard, Genetics 1954, 39:440–452) by the method of Hagemann (Gentechnologische.Arbeitsmethoden [Genetic Engineering.Working Methods], Gustav Fischer Verlag, 1990: 14–18).The suspension with the λ::Tn5 lysate was incubated at 30° C. for 45 minutes. After centrifugation at 3000 rpm for 5 minutes, the pellet was taken up in 10 ml PA+10 mM pyrophosphate and incubated at 37° C. for 3 hours. The bacteria solution was plated out as a dilution series on medium E agar+glucose (0.4%)+25 µg/ml kanamycin+50 µg/ml isoleucine+50 µg/ml ketoisovalerate+50 µg/ml pantothenate and incubated at 37° C. for 48 hours. Individual colonies were inoculated in parallel on medium E agar+glucose (0.4%)+25 µg/ml kanamycin+50 µg/ml isoleucine+50 µg/ml ketoisovalerate+50 µg/ml pantothenate and on medium E agar+glucose (0.4%)+25 µg/ml kanamycin+50 µg/ml isoleucine+50 µg/ml ketoisovalerate and incubated at 37° C. for 48 hours. Among 14000 individual colonies inoculated, it was possible to identify one, called FE5, colony which grew on medium E agar+glucose (0.4%)+25 µg/ml kanamycin+50 µg/ml isoleucine+50 µg/ml ketoisovalerate+50 µg/ml pantothenate but not on medium E agar+glucose (0.4%)+25 µg/ml kanamycin+50 µg/ml isoleucine+50 µg/ml ketoisovalerate.

3. Characterization of the strains FE4 and FE5

Together with the *E. coli* strains SJ2 (Jakowski, Genetic Stock Center, Yale University),which carries a mutation in the panB gene, MW6 (Williams, Genetic Stock Center, Yale University), which carries a mutation in the panC gene, and DV9 (Vallari, Journal of Bacteriology 1985, 164:136–142), which carries a mutation in the panD gene, and a wild type, the strains FE4 and FE5 were smeared on to various supplemented base media (medium E agar+glucose (0.4%)+50 µg/ml isoleucine+50 µg/ml ketoisovalerate; and in the case of SJ2, DV9 and MW6 additionally 50 µg/ml thiamine) and were incubated at 37° C. for 48 hours. Pantothenate (calcium salt), ketopantoate (sodium salt), β-alanine (Sigma (Deisenhofen, Germany), Code no. A7752) and pantoate (potassium salt) were used as additional supplements. Ketopantoate was prepared from ketopantolactone by treatment with equimolar amounts of NaOH at 60° C. and subsequent evaporation. Ketopantolactone was synthesized by the method of Ojima et al. (Organic Synthesis 63, 18 (1985)). Pantoate was prepared from pantoyllacton (Sigma (Deisenhofen, Germany), Code no. P2625) by the method of Primerano and Burns (Journal of Bacteriology 1983, 153:259–269). The result of the growth test (table 1) showed that the strain FE4 grew on all the base media with various supplements. The strain FE5 grew only on media which were supplemented with either pantothenate or pantoate, but not on base media to which ketopantoate was added.

TABLE 1

| Strain | Supplements in the base medium | | | | |
| --- | --- | --- | --- | --- | --- |
| | none | β-Alanine [50 µg/ml] | Ketopantoate [50 µg/ml] | Pantoate [50 µg/ml] | Pantothenate [50 µg/ml] |
| MG1655 | + | + | + | + | + |
| SJ2 | − | − | + | + | + |
| MW6 | − | − | − | − | + |
| DV9 | − | + | − | − | + |
| FE4 | + | + | + | + | + |
| FE5 | − | − | − | + | + |

+ = growth
− = no growth

EXAMPLE 2

Isolation of the panE gene from *Escherichia coli* K12 Strain W1485

The *E. coli* K12 W1485 MATCHMAKER Genomic Library (CLONTECH (Heidelberg, Germany), Cat. no. XL4001AB) was electroporated into the strain FE5. The *E. coli* K 12 MATCHMAKER Genomic Library contains the chromosomal DNA of *E. coli* K12 W1485 as inserts on average 1.0 kbp in size in the plasmid pGAD10, the size of the individual inserts here varying from 0.5–3.0 kbp (CLONTECH (Heidelberg, Germany)). The transformants were selected by plating out on medium E agar+glucose (0.4%)+100 µg/ml ampicillin+50 µg/ml isoleucine+50 µg/ml ketoisovalerate. The plasmid DNA was isolated from 20 resulting colonies with the aid of the QIAprep Spin Plasmid Kit. By an EcoRI cleavage of the plasmid DNA and subsequent separation in 0.8% agarose gel (30 minutes, 10V/cm), it was shown that the plasmids were 20 pGAD10 vectors with inserts of different sizes. Sequencing (IIT Biotech (Bielefeld, Germany)) of the inserts showed, by homology comparisons with the BLAST program (Altschul, Journal of Molecular Biology 1990, 215: 403–410), that in 7 cases the inserts contained a complete ilvC gene and in 13 cases an open reading frame, which was described as "similar to *Salmonella typhimurium* apbA" (EMBL-GenBank: Accession No. U82664). This open reading frame was called panE.

EXAMPLE 3

Over-expression of the ilvC gene of *E. coli* in *E. coli* K12 Strain MG1655

For over-expression of the ilvC gene, plasmid pFE32 (see example 1) was used. In plasmid pFE32, the coding region of the ilvC gene is under the control of the tet promoter coded by plasmid pBR322. Plasmid pFE32 was electroporated into the strain *E. coli* K12 MG1655 and transformants were selected on LB agar, after subsequent incubation at 37° C. for 24 hours, to which 100 µg/ml ampicillin was added. The resulting strain was called MG 1655/pFE32.

EXAMPLE 4

Over-expression of the panE gene of *E. coli* in *E. coli* K12 Strain MG1655

Starting from the nucleotide sequence for the panE gene in *E. coli* K12 MG1655, PCR primers were synthesized (MWG Biotech (Ebersberg, Germany)). A DNA fragment approximately 1000 bp in size could be amplified from chromosomal *E. coli* K12 MG1655 DNA with these primers by the standard PCR method. The chromosomal *E. coli* K12 MG1655 DNA employed for the PCR was isolated by means of the NucleoSpin C+T Kit. The size was determined by separation by gel electrophoresis (30 minutes, 10V/cm) in a 0.8% agarose gel.

PCR primers for the panE gene from *E. coli*:

```
panE1 5'- AGGAGGACAATGAAAATTAC -3'    (SEQ ID NO:3)

panE2 5'- TCAGTCTCTTCACTACCAGG -3'    (SEQ ID NO:4)
```

The PCR product of the pan E gene was transformed into the plasmid pCR®2.1 and into *E. coli* strain TOP10F' (Invitrogen (Leek, The Netherlands), Product Description Original TA Cloning® Kit, Cat. no. KNM2030-01). Successful cloning was demonstrated by cleavage of the DNA of the plasmid pCR®2.1 panE with the restriction enzymes EcoRI and HincII (Pharmacia Biotech (Freiburg, Germany), Product Description HincII, Code no. 27-0858-01). For this, the plasmid DNA was isolated by means of the QIAprep Spin Plasmid Kit and, after cleavage, separated in a 0.8% agarose gel (30 minutes, 10V/cm).

To isolate the panE gene from the plasmid pCR®2.1 panE the plasmid DNA isolated was cleaved with the enzyme EcoRI, the cleavage batch was separated in 0.8% agarose gel (30 minutes, 10V/cm) and the 1.0 kbp panE fragment was isolated with the aid of the GLASSMAX™ Kit. The panE fragment isolated was ligated with the plasmid pKK223-3, also cleaved with EcoRI, by means of T4 DNA ligase and the *E. coli* strain DH5αmcr was electroporated with the ligation batch. Selection for plasmid-carrying cells was carried out by plating out the electroporation batch on LB agar, to which 100 µg/ml ampicillin was added, and subsequent incubation at 37° C. for 24 hours. The required plasmid could be identified, after isolation of the DNA and checking of the cleavage, with the enzymes EcoRI and HincII in one clone by subsequent gel electrophoresis in 0.8% agarose gel (30 minutes, 10V/cm), and was called pFE65.

In plasmid pFE65, the coding region of the panE gene is under the control of the tac promoter coded by plasmid pKK223-3. Plasmid pFE65 was electroporated into the strain *E. coli* K12 MG1655 and transformants were selected on LB agar, to which 100 µg/ml ampicillin was added, and subsequent incubation for 24 hours at 37° C. The resulting strain was called *E. coli* K12 MG1655/pFE65.

EXAMPLE 5

Over-expression of the panE gene of *E. coli* Together With panB, panC and panD of *E. coli* in *E. coli* K12 Strain MG1655.

Starting from the nucleotide sequence for the panB gene, panC gene and panD gene in *E. coli* K12 MG1655, (EMBL-GenBank: Accession No. L17086), PCR primers were synthesized (MWG Biotech (Ebersberg, Germany)). From chromosomal *E. coli* K12 MG1655 DNA, a DNA fragment approximately 800 bp in size could be amplified with the panB primers, and a DNA fragment approximately 400 bp in size could be amplified with the panD primers, using the standard PCR method. A DNA fragment approx. 850 bp in size could be amplified from chromosomal *E. coli* K12 MG1655 DNA with the panC primers by means of a modified standard PCR method. Taq polymerase was replaced by Pfu polymerase and the buffer conditions in the PCR batch were modified accordingly (STRATAGENE (Heidelberg, Germany), Product Description Pfu Polymerase, Code no. 600135). The chromosomal *E. coli* K12 MG1655 DNA employed for the PCR was isolated by means of the NucleoSpin C+T Kit The size of all the amplified products was determined by separation by gel electrophoresis (30 minutes, 10V/cm) in a 0.8% agarose gel.

PCR primers for the panB gene from *E. coli*:

```
panB1 5'- AGGATACGTTATGAAACCGA -3'    (SEQ ID NO:5)

panB2 5'- ACAACGTGACTCCTTAATGG -3'    (SEQ ID NO:6)
```

PCR primers for the panC gene from *E. coli*:

```
panC1 5'- AGGAGTCACGTTGTGTTAAT -3'    (SEQ ID NO:7)

panC2 5'- AAGTATTACGCCAGCTCGAC -3'    (SEQ ID NO:8)
```

PCR primers for the panD gene from *E. coli*:

```
panD1 5'- AGGTAGAAGTTATGATTCGC -3'    (SEQ ID NO:9)

panD2 5'- TAACAATCAAGCAACCTGTA -3'    (SEQ ID NO:10)
```

The PCR product of the panB gene was transformed into the plasmid pCR®82.1 and into the *E. coli* strain TOP10F' (Invitrogen (Leek, The Netherlands). Successful cloning of the panB PCR product was demonstrated by cleavage of the DNA of the plasmid pCR®2.1 panB with the restriction enzymes EcoRI, EcoRV (Pharmacia Biotech (Freiburg, Germany), Product Description EcoRV, Code no. 27-0934-01) and PvuII (Pharmacia Biotech (Freiburg, Germany), Product Description PvuII, Code no. 27-0960-01). For this, the plasmid DNA was isolated by means of the QIAprep Spin Plasmid Kit and, after cleavage, separated in a 0.8% agarose gel (30 minutes, 10V/cm). The PCR product of the panD gene was transformed into the plasmid pCR®2.1 and into the *E. coli* strain TOP10F' (Invitrogen (Leek, The Netherlands). Successful cloning of the panD PCR product was demonstrated by cleavage of the DNA of the plasmid pCR®2.1 panD with the restriction enzymes EcoRI, EcoRV and HincII. For this, the plasmid DNA was isolated by means of the QIAprep Spin Plasmid Kit and, after cleavage, separated in a 0.8% agarose gel (30 minutes, 10V/cm). The PCR product of the panC gene was electroporated into the plasmid pUC19 (Viera, Gene 1982 19:259–268) and into the *E. coli* strain DH5αmcr. Successful cloning of the panC PCR product was demonstrated by cleavage of the DNA of the plasmid pUC19panC with the restriction enzymes EcoRI, HindIII and SalI (Pharmacia Biotech (Freiburg, Germany), Product Description SalI, Code no. 27-0882-01). For this, the plasmid DNA was isolated by means of the QIAprep Spin Plasmid Kit and, after cleavage, separated in a 0.8% agarose gel (30 minutes, 10V/cm). The plasmid constructed was called pFE60.

To isolate the panB gene from the plasmid pCR®2.1panB the plasmid DNA isolated was cleaved with the enzyme EcoRI, the cleavage batch was separated in 0.8% agarose gel (30 minutes, 10V/cm) and the 800 bp panB fragment was isolated with the aid of the GLASSMAX™ Kit. The panB fragment isolated was ligated with the plasmid pKK223-3, also cleaved with EcoRI, by means of T4 DNA ligase and the *E. coli* strain DH5αmcr was electroporated with the ligation batch. Selection for plasmid-carrying cells was carried out by plating out the electroporation batch on LB agar, to which 100 μ/ml ampicillin was added, and subsequent incubation at 37° C. for 24 hours. The required plasmid could be identified, after isolation of the DNA and checking of the cleavage, with the restriction enzymes EcoRI, EcoRV and PvuII in one clone by subsequent gel electrophoresis in 0.8% agarose gel (30 minutes, 10V/cm), and was called pFE40. In plasmid pFE40, the coding region of the panB gene is under the control of the tac promoter coded by plasmid pKK223-3.

To isolate the panD gene from the plasmid pCR®2.1panD the plasmid DNA isolated was cleaved with the enzyme EcoRI, the cleavage batch was separated in 0.8% agarose gel (30 minutes, 10V/cm) and the 400 bp panD fragment was isolated with the aid of the GLASSMAX™ Kit. The panD fragment isolated was ligated with the plasmid pKK223-3, also cleaved with EcoRI, by means of T4 DNA ligase and the *E. coli* strain DH5αmcr was electroporated with the ligation batch. Selection for plasmid-carrying cells was carried out by plating out the electroporation batch on LB agar, to which 100 μg/ml ampicillin was added, and subsequent incubation at 37° C. for 24 hours. The required plasmid could be identified, after isolation of the DNA and checking of the cleavage, with the enzymes EcoRI, EcoRV and HincII in one clone by subsequent gel electrophoresis in 0.8% agarose gel (30 minutes, 10V/cm), and was called pFE50. In plasmid pFE50, the coding region of the panD gene is under the control of the tac promoter coded by plasmid pKK223-3.

The panC gene was isolated from the plasmid pFE60 by means of a HindIII-SmaI (Pharmacia Biotech (Freiburg, Germany), Product Description SmaI, Code no. 27-0942-01) cleavage, for which the cleavage batch was separated in 0.8% agarose gel (30 minutes, 10V/cm) and the 850 bp panC fragment was isolated with the aid of the GLASSMAX™ Kit. The panC fragment isolated was ligated with the plasmid pFE50, also cleaved with HindIII and SmaI, by means of T4 DNA ligase and the *E. coli* strain DH5αmcr was electroporated with the ligation batch. Selection for plasmid-carrying cells was carried out by plating out the electroporation batch on LB agar, to which 100μg/ml ampicillin was added, and subsequent incubation at 37° C. for 24 hours. The required plasmid could be identified, after isolation of the DNA and checking of the cleavage, with the enzymes EcoRI, EcoRV, SmaI, HindIII and HincII in one clone by subsequent gel electrophoresis in 0.8% agarose gel (30 minutes, 10V/cm), and was called pFE52. In plasmid pFE52, the coding regions of the panD gene and of the panC gene are under the control of the tac promoter coded by plasmid pKK223-3 and form an operon.

The panB gene was cloned into the EcoRI cleavage site of plasmid pFE52 following the tac promoter, and the resulting plasmid was called pFE70. For this, the panB gene was isolated from an agarose gel (30 minutes, 10V/cm) in which an EcoRI restriction batch of the plasmid pFE40 was separated. Ligation was carried out with T4 DNA ligase. After electroporation of the ligation batch into the strain SJ2, the transformants were selected on mediumE agar, to which 0.4% glucose, 100 μg/ml thiamine and 100 μg/ml ampicillin were added. DNA from ampicillin-resistan colonies was isolated with the QIAprep Spin Plasmid Kit and successful cloning was verified by means of an EcoRI, EcoRV, SmaI, HindIII and HincII cleavage and subsequent separation in 0.8% agarose gel (30 minutes, 10V/cm). In plasmid pFE70, the coding regions of the panB gene, panD gene and of the panC gene are under the control of the tac promoter coded by plasmid pKK223-3 and form an operon.

The panE gene was isolated from the plasmid pFE65 by means of a HindIII-SphI (Pharmacia Biotech (Freiburg, Germany), Product Description SphI, Code no. 27-0951-01) cleavage, for which the cleavage batch was separated in 0.8% agarose gel (30 minutes, 10V/cm) and the panE fragment was isolated with the aid of the GLASSMAX™ Kit. The panE fragment isolated was ligated with the plasmid pFE70, also cleaved with HindIII and partly with SphI, by means of T4 DNA ligase and the strain FE5 was electroporated with the ligation batch. Selection for plasmid-carrying cells was carried out by plating out the electroporation batch on mediaE agar+glucose (0.4%)+50 μg/ml isoleucine+50 μg/ml ketoisovalerate, to which 100 μg/ml ampicillin was added, and subsequent incubation at 37° C. for 48 hours. The required plasmid could be identified, after isolation of the DNA and checking of the cleavage, with the enzymes EcoRI, EcoRV, SphI, HindIII and HincII in one clone by subsequent gel electrophoresis in 0.8% agarose gel (30 minutes, 10V/cm), and was called pFE80. In plasmid pFE80, the coding regions of the panB gene, panD gene, panC gene and of the panE gene are under the control of the tac promoter coded by plasmid pKK223-3 and form an operon.

Plasmid pFE80 was electroporated into the strain *E. coli* K12 MG 1655 and transformants were selected on LB agar, to which 100 μg/ml ampicillin was added, and subsequent incubation for 24 hours at 37° C. The resulting strain was called MG1655/pFE80.

EXAMPLE 6

Over-expression of the panE gene of *E. coli* Together with panB, panC and panD of *E. coli* in a Valine-resistant Mutant of *E. coli* K12 MG1655.

The *E. coli* K12 strain MG1655 was smeared on to mediumE agar, to which 0.4% glucose and 100 μg/ml valine (Sigma (Deisenhofen, Germany),V0258) were added. After incubation at 37° C. for 48 hours, a colony could be isolated.

This strain was called FE6. Plasmid pFE80 was electroporated into the strain FE6 and transformants were selected on LB agar, to which 100 μg/ml ampicillin was added, and subsequent incubation for 24 hours at 37° C. The resulting strain was called FE6/pFE80.

EXAMPLE 7

Over-expression of the panE gene of *E. coli* Together With panB, panC and panD of *E. coli* in an avtA::aadB Mutant of *E. coli* K12 MG1655.

Starting from the nucleotide sequence for the avtA gene (EMBL-GenBank: Accession No. Y00490) in *E. coli* K12 MG1655, PCR primers were synthesized (MWG Biotech (Ebersberg, Deutschland)). A DNA fragment approx. 1.6 kbp in size could be amplified from chromosomal *E. coli* K12 MG1655 DNA with these primers by the standard PCR method. The size was determined by separation by gel electrophoresis (30 minutes, 10V/cm) in a 0.8% agarose gel.

PCR primers for the avtA gene from *E. coli*:

```
avtA1 5'- TGCTCTCTCTCAACGCCGAA -3'   (SEQ ID NO:11)
avtA2 5'- GAAGCCGCCAACCAGGATAA -3'   (SEQ ID NO:12)
```

The PCR product of the avtA gene was transformed into the plasmid pCR®2.1 and into the *E. coli* strain TOP10F' (Invitrogen (Leek, The Netherlands)). Successful cloning was demonstrated by cleavage of the DNA of the plasmid pCR®2.1 avtA with the restriction enzymes EcoRI and SmaI. For this, the plasmid DNA was isolated by means of the QIAprep Spin Plasmid Kit and, after cleavage, separated in a 0.8% agarose gel (30 minutes, 10V/cm). An aadB gene was cloned into the SmaI cleavage site of plasmid pCR®2.1 actA and the resulting plasmid was called pFE23. For this, the aadB gene was isolated from an agarose gel (30 minutes, 10V/cm) in which an SmaI restriction batch of the plasmid pHP45Ω (EMBL-GenBank: Accession No. K02163) was separated. Ligation was carried out with T4 DNA ligase. After electroporation of the ligation batch into the strain DH5αmcr, the transformants were selected on PA agar, to which 20 μg/ml streptomycin (Sigma (Deisenhofen, Germany), Code no. S6501 ) was added. DNA from streptomycin-resistant colonies was isolated with the QIAprep Spin Plasmid Kit and successful cloning was verified by means of an EcoRI and SphI cleavage and subsequent separation in 0.8% agarose gel (30 minutes, 10V/cm).

The avtA::aadB fragment was cleaved out of the plasmid pFE23 by means of EcoRI restriction, separated in 0.8% agarose gel (30 minutes, 10V/cm) and isolated with the GLASSMAX™ Kit. The fragment was ligated with the plasmid pMAK705, which was partly cleaved with EcoRI, by means of T4 DNA ligase, the ligation batch was electroporated into the strain DH5αmcr and transformants were selected by incubation on LB agar+20 μg/ml streptomycin+ 25 μg/ml chloramphenicol for 24 hours at 30° C. DNA from streptomycin- and chloramphenicol-resistant colonies was isolated with the QIAprep Spin Plasmid Kit and successful cloning was verified by means of an SphI and EcoRI cleavage in 0.8% agarose gel (30 minutes, 10V/cm). The plasmid constructed was called pFE24.

The chromosomal avtA gene in the strain *E. coli* K12 MG1655 was exchanged for the avtA::aadB allele with the aid of the plasmid pFE24. A modified method according to Hamilton et al. was used for the gene exchange. Plasmid pFE24 was electroporated into the *E. coli* K12 MG1655 strain, and the transformants were then incubated on LB-chloramphenicol agar at 42° C. for 24 hours for selection for cointegrates. For individualization, the resulting colonies were in turn smeared on the same medium and incubated at 42° C. for 24 hours. For disintegration of the plasmid, individual colonies were incubated in 5 ml LB liquid medium at 42° C. for 24 hours, and a dilution series of the liquid medium was then plated out on LB-chloramphenicol agar. This dilution series was incubated at 30° C. for 24 hours. For curing of the plasmid, individual colonies obtained from the dilution series were cultured in 3 successive individual colony smears on LB agar at 42° C. for in each case 24 hours.

To check the phenotype, the resulting individual colonies were inoculated in parallel on agar plates with LB medium+ 20 μg/ml streptomycin and LB medium+25 μg/ml chloramphenicol. These media were incubated at 37° C. for 48 hours. Of 250 individual colonies tested, there was one of which the phenotype displayed the exchange of the chromosomal avtA gene for the avtA::aadB fragment. This strain was called FE7.

Plasmid pFE80 was electroporated into the strain FE7 and transformants were selected on LB agar, to which 100 μg/ml ampicillin was added, and subsequent incubation for 24 hours at 37 2° C. The resulting strain was called FE7/pFE80.

EXAMPLE 8

Determination of the Ketopantoate Reductase Activity in Various Strains of *Escherichia coli* K12.

The specific ketopantoate reductase activity was determined by the method described by Shimizu et al. (Journal of Biological Chemistry 263:12077–12084 (1988)). For this, cell extracts of the individual strains were obtained by means of a Hybaid RiboLyser (Heidelberg, Germany) and the RiboLyser Kit Blue. The ketopantoate reductase activity of the extracts was determined with the aid of the NADPH consumption on addition of ketopantoate. The specific ketopantoate reductase activity determined was 6.5 mU/mg for the strain *E. coli* K12 MG1655, and 22.0 mU/mg for the strain *E. coli* K12 MG1655/pFE65. In the case of strain FE5, no activity was measurable.

EXAMPLE 9

Formation of Pantothenate by Various Strains of *Escherichia coli* K12

The formation of pantothenate by the strains MG1655, MG1655/pFE32, MG 1655/pFE65, MG 1655/pFE80, FE6/ pFE80 and FE7/pFE80 was investigated in a batch culture. The culture medium used was the medium E described by Vogel (Journal of Biological Chemistry 1956, 218:97–106) with glucose (0.4%) as the source of carbon. The composition of the medium used is shown in Table 2.

TABLE 2

| Compound | Concentration |
| --- | --- |
| $MnSO_4 * 7H_2O$ | 0.2 g/l |
| Citric acid monohydrate | 2.0 g/l |
| $K_2HPO_4$ | 10.0 g/l |
| $NaNH_4HPO_4 * H_2O$ | 3.5 g/l |

250 ml conical flasks were filled with 25 ml of the stated nutrient medium and the batch was inoculated. After an incubation time of 48 hours at 37° C., the optical density and the pantothenate concentration were determined. For determination of the cell density, the optical density with a Novaspec II Photometer photometer from Pharmacia (Freiburg, Germany) at a measurement wavelength of 580 nm was employed. The pantothenate content was determined in the sterile-filtered culture supernatant. The pantothenate (as the calcium salt) was determined with the aid of the strain Lactobacillus plantarum ATCC® 8014 as described in the handbook "DIFCO MANUAL" from DIFCO (Michigan, USA;, 10$^{th}$ Edition, 1100–1102 (1984)). The result is summarized in Table 3.

TABLE 3

| Strain | Concentration [µg/ml] | Cell density [OD$_{580}$] | Productivity [µg/ml/OD$_{580}$] |
|---|---|---|---|
| MG1655 | 0.51 | 2.8 | 0.18 |
| MG1655/pFE32 | 1.7 | 2.8 | 0.60 |
| MG1655/pFE65 | 4.6 | 2.9 | 1.6 |
| MG1655/pFE80 | 14.0 | 2.9 | 4.8 |
| FE6/pFE80 | 35.7 | 3.2 | 11.2 |
| FE7/pFE80 | 41.7 | 3.0 | 13.9 |

EXAMPLE 10

Formation of pantothenate by Various strains of Escherichia coli K12 in the Presence of ketopantoate The formation of pantothenate by the strains MG1655, MG1655/pFE32, MG1655/pFE65 with added ketopantoate was investigated in a batch culture. For this, the medium described in example 8 was supplemented with 50 µg/ml ketopantoate. The other conditions of the experiment are as described in example 8. The result is shown in Table 4.

TABLE 4

| Strain | Concentration [µg/ml] | Cell density [OD$_{580}$] | Productivity [µg/ml/OD$_{580}$] |
|---|---|---|---|
| MG1655 | 6.2 | 2.9 | 2.1 |
| MG1655/pFE32 | 9.0 | 2.9 | 3.1 |
| MG1655/pFE65 | 12.6 | 2.9 | 4.3 |

EXAMPLE 11

Isolation of the ilvC gene of Corynebacterium glutamicum ATCC13032

Chromosomal DNA from C. glutamicum ATCC 13032 was isolated as described by Tauch et al. (Plasmid, 33:168–179,1995) and partly cleaved with the restriction enzyme Sau3A (Pharmacia Biotech (Freiburg, Germany), Product Description Sau3A, Code no. 27-0913-02). DNA fragments in a size range of 7–9 kb were isolated with the aid of the "Nucleotrap Extraction Kit for Nucleic Acids" (Macherey und Nagel, Düren, Germany; Cat. No. 740584) and ligated into the dephosphorylated BamHI cleavage site of the vector pUC19 (Viera et al., 1982, Gene, 19:259–268; MBI Fermentas, Lithuania). The ligation was carried out as described by Sambrook et al. (1989, Molecular Cloning: A laboratory Manual, Cold Spring Harbor), the DNA mixture being incubated overnight with T4 ligase (Pharmacia Biotech, Freiburg, Germany). This ligation mixture was then electroporated into the E. coli strain DH5aMCR (Grant, 1990, Proceedings of the National Academy of Sciences U.S.A., 87:4645–4649; Tauch, 1994, FEMS Microbiological Letters, 123:343–348) and plated out on LB agar (Lennox, 1955, Virology, 1:190)+100 mg/ml ampicillin. After incubation for 24 h at 37° C., the C. glutamicum gene library could be obtained from the transformants by re-isolation of the plasmid DNA by the "alkaline lysis method" of Birnboim and Doly (1997, Nucleic Acids Research, 7:1513–1523).

Competent cells of the E. coli strain FE5, which carries mutations in the panE and ilvC gene, were electroporated with this gene library. After the regeneration phase (Tauch et.al., 1994, FEMS Microbiological Letters, 123:343–347), the electroporation batch was washed twice with medium E (Vogel and Bonner, 1956, Journal of Biological Chemistry, 218:97–106). The transformants were selected by plating out on medium E agar+glucose (0.4%)+100 µg/ml ampicillin+50 µg/ml isoleucine+50 µg/ml ketoisovalerate. The plasmid DNA was isolated from 4 resulting colonies with the aid of the QIAprep Spin Plasmid Kit. By an XbaI cleavage of the plasmid DNA and subsequent separation in 0.8% agarose gel (30 minutes, 10V/cm), it was shown that the plasmids were pUC19 vectors with inserts approximately 6.5 kbp in size. Sequencing of the inserts with subsequent homology comparisons with the aid of the BLAST program (Altschul, Journal of Molecular Biology 1990, 215:403–410) showed that in all cases the inserts contained a complete ilvC gene from C. glutamicum (EMBL-GenBank: Accession No. L09232). One of these plasmids was called pFE90.

EXAMPLE 12

Expression of the ilvC Gene of Corynebacterium glutamicum ATCC13032 in Corynebacterium glutamicum ATCC13032

The plasmid pECm3 was used for expression of the ilvC gene from C. glutamicum in C. glutamicum ATCC13032. Plasmid pECm3 is a derivative of plasmid pECm2 (Tauch, 1994, FEMS Microbiological Letters, 123:343–348), the kanamycin resistance gene of which has been removed by a BgIII (Pharmacia Biotech (Freiburg, Germany), Product Description BgIII, code no. 27-0946-02)and BamHI restriction with subsequent re-ligation. The plasmids pECm2 and pECm3 are capable of replication both in E. coli and in C. glutamicum. To isolate the ilvC gene from the plasmid pFE90 (example 11), the plasmid DNA isolated was cleaved with the enzyme XbaI (Pharmacia Biotech (Freiburg, Germany), Product Description XbaI, Code no. 27-0948-01), the cleavage batch was separated in 0.8% agarose gel (30 minutes, 10V/cm) and the 6.5 kbp ilvC fragment was isolated with the aid of the GLASSMAX™ Kit. The ilvC fragment isolated was ligated with the plasmid pECm3, also cleaved with XbaI, by means of T4 DNA ligase and E. coli strain FE5 was electroporated with the ligation batch. Selection for plasmid-carrying cells was carried out by plating out the electroporation batch on LB agar, to which 50 µg/ml chloramphenicol was added, and subsequent incubation at 37° C. for 24 hours. The required plasmid could be identified, after isolation of the DNA and checking of the cleavage, with the enzyme Xba in one clone by subsequent gel electrophoresis in 0.8% agarose gel (30 minutes, 10 V/cm), and was called pFE91.

Plasmid pFE91 was electroporated into the strain C. glutamicum ATCC13032 and transformants were selected on LB agar, to which 75 µg/ml chloramphenicol was added, and subsequent incubation for 48 hours at 302° C. The resulting strain was designated C. glutamicum ATCC13032/pFE91.

EXAMPLE 13

Formation of Pantothenate by Corynebacterium glutamicum ATCC13032

The formation of pantothenate by the C. glutamicum strain ATCC13032/pFE91 was investigated in medium CGXII (Keilhauer et al., 1993, Journal of Bacteriology, 175:5595–5603) with 10 mg/ml chloramphenicol (referred to as "*C. glutamicum* test medium" in the following). This medium is shown in Table 5. In each case 50 ml of freshly prepared *C. glutamicum* test medium were inoculated with a 16 hours old culture (*C. glutamicum* test medium 302° C., 150 rpm) with an $OD_{580}$ of 0.1. After incubation at 30° C. and 150rpm for 48 hours, the cells were removed by centrifugation at 5000×g for 10 minutes, the supernatant was sterile-filtered and the pantothenate concentration was determined. The cell density was determined as described in example 9.

The pantothenate (as the calcium salt) was determined with the aid of the strain *Lactobacillus plantarum* ATCC® 8014 as described in the handbook "DIFCO MANUAL" from DIFCO (Michigan, USA;,10$^{th}$ Edition, 1100–1102 (1984)). The result is shown in Table 6.

TABLE 5

| Substance | Amount per liter | Comments |
|---|---|---|
| $(NH_4)_2SO_2$ | 20 g | |
| Urea | 5 g | |
| $KH_2PO_4$ | 1 g | |
| $K_2HPO_4$ | 1 g | |
| $MgSO_4*7H_2O$ | 0.25 g | |
| MOPS | 42 g | |
| $CaCl_2$ | 10 mg | |
| $FeSO_4*7H_2O$ | 10 mg | |
| $MnSO_4*H_2O$ | 10 mg | |
| $ZnSO_4*7H_2O$ | 1 mg | |
| $CuSO_4$ | 0.2 mg | |
| $NiCl_2*6H_2O$ | 0.02 mg | |
| Biotin | 0.5 mg | |
| Glucose | 40 g | autoclave separately |
| Protocatechuic acid | 0.03 mg | sterile-filter |

TABLE 6

| Strain | Concentration [µg/ml] | Cell density [$OD_{580}$] | Productivity [µg/ml/$OD_{580}$] |
|---|---|---|---|
| ATCC13032 | 0.2 | 20 | 0.010 |
| ATCC13032/pFE91 | 0.3 | 20 | 0.015 |

EXAMPLE 14:

Expression of the panE Gene of *Saccharomyces cerevisiae*

1. Amplification of the reading frame YHR063c:

Starting from the nucleotide sequence of the *Saccharomyces cerevisiae* reading frame YHR063c (Accession No. U00061 of the National Center for Biotechnology, Bethesda, Md., USA) the following PCR primers were synthesized (MWG-Biotech, Ebersberg, Germany). The start and end of the reading frame are identified by a dot (.):

oJD539 (5' EcoRI-NotI START): 5'- GCG CGA ATT CAG ATC CGC GGC CGC AAA GAG GAG AAA TTA ACT.ATG ACT GCA CCA CAC AGA AG-3' (SEQ ID NO: 13)

oJD540 (3' SpeI-PstI STOP): 5'- CGC GAC TAG TCT GCA G.TC AGT CCT TTC TCC AGT CAC-3'(SEQ ID NO: 14)

Genomic DNA of the *S. cerevisiae* strain JD242, which was isolated by the method of C. Guthrie and G. R. Fink (Guide to yeast genetics and molecular biology, Methods in Enzymology, Vol. 194, Academic Press, San Diego, Calif., 1991), was used as the template. This strain is a haploid segregant of the diploid strain SC288C. (Winston et al., Yeast 11, 53 et seq. (1995)), the genome of which has been sequenced (Goffeau et al., Science 274, pp. 546, (1996)).

The tetrad analysis was carried out by the method of C. Guthrie and G. R. Fink (Guide to yeast genetics and molecular biology, Methods in Enzymology, Vol. 194, Academic Press, San Diego, Calif., 1991). The strain JD242 is auxotrophic for leucine (leu2Al allele) and uracil (ura3–52 allele). A DNA fragment about 1.2 kb in size could be amplified using the "High Fidelity Expand Polymerase" Kit from Roche (Mannheim) by 28 PCR cycles under the conditions described by the manufacturer. The size was determined by separation by electrophoresis in a 0.8% agarose gel.

Figure 8:
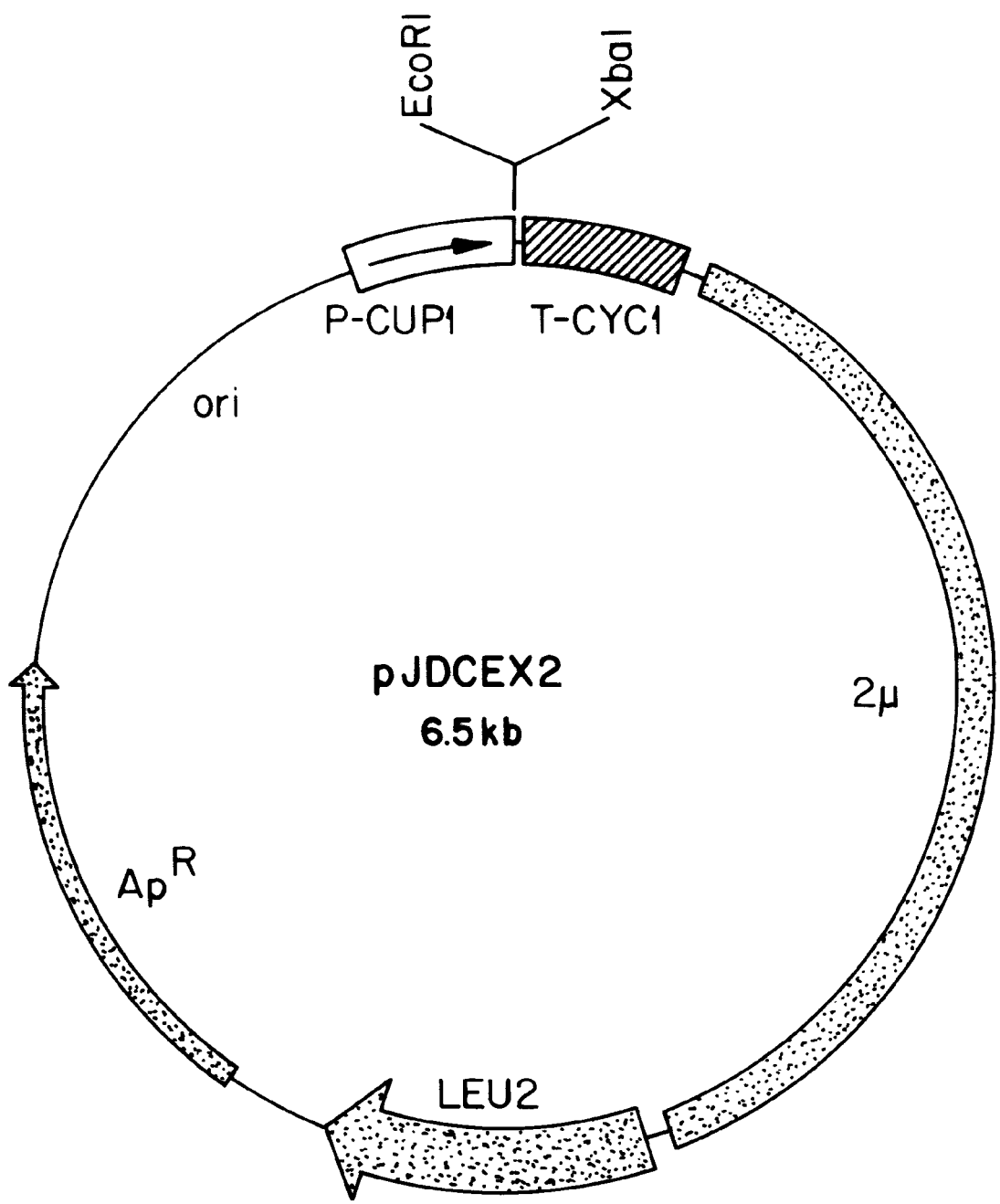
FIG. 8: Map of the plasmid pJDCEX2.

2. Construction of pJD-YHR063c:

For expression of the YHR063c reading frame in *S. cerevisiae*, the product amplified by PCR was incorporated into the *E. coli-S. cerevisiae* shuttle vector pJDCEX2 (FIG. 8 and Dohmen et al., 1995, Journal of Biological Chemistry 270, 18099–18109).

Figure 9:
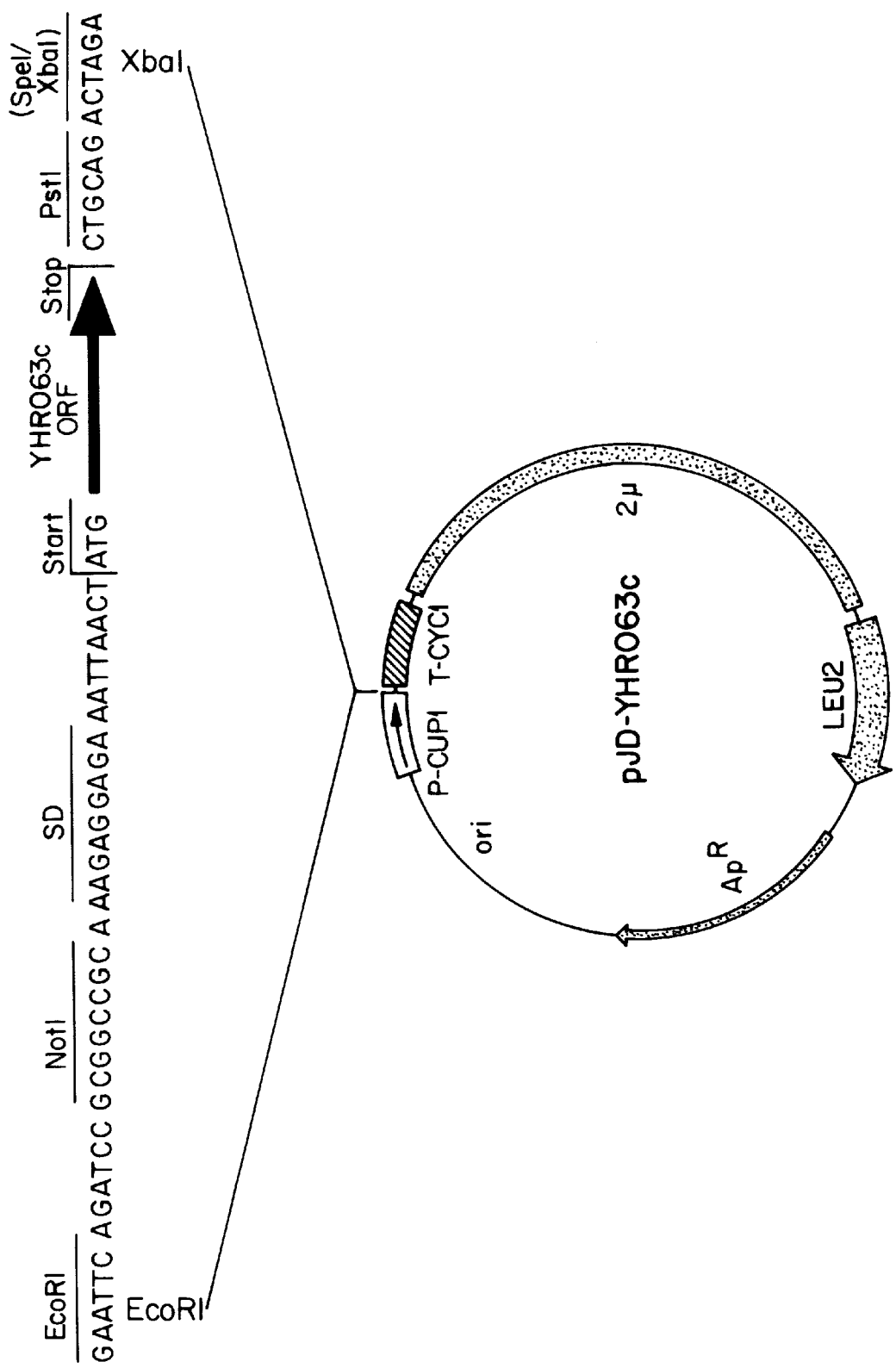
FIG. 9: Map of the plasmid pJD-YHR063c including SEQ ID NO: 17 and SEQ ID: 18 adjacent to the YHR063c open reading frame.

The PCR product was first restricted with EcoRI and SpeI (AGS, Heidelberg, Germany). It was then mixed with pJDCEX2-DNA, which had been treated with EcoRI and XbaI (AGS, Heidelberg, Germany), and ligated with T4 DNA ligase (Roche, Mannheim, Germany). The ligation batch was transformed into the *E. coli* strain XL1 -Blue (Bullock et al., 1987, Biotechniques 5, 376). Transformants were obtained by selection on LB agar comprising 150 µg/ml ampicillin (Sigma (Deisenhofen, Germany). Plasmid DNA from the ampicillin-resistant clones was prepared by alkaline lysis (Sambrook et al.: Molecular Cloning, A Laboratory Manual, Cold Spring Harbor Laboratory Press, 1989). The plasmid DNA isolated was then investigated by restriction with NotI and PstI and subsequent separation in 0.8% agarose gel. The plasmid with the desired structure was given the name pJD-YHR063c (FIG. 9). The sequence of the PCR product cloned in pJD-YHR063c was verified by sequencing with the oligonucleotides oJD105 and oJD106.

oJD105 (T-CYC1): 5'-GAAGTCATCGAAATAG-3' (SEQ ID NO: 15)

oJD106 (P-CUP1): 5'-TCGTTTCTGCTTTTTC-3' (SEQ ID NO: 16)

3. Construction of pKK-YHR063c:

The plasmid pKK223-3 (Brosius and Holy, Proceedings of the National Academy of Science USA 81, 6929 (1984) was used for expression of the YHR063c reading frame *E. coli*. For this, the plasmid pJD-YHR063c was first restricted with EcoRI and PstI (AGS, Heidelberg, Germany). After electrophoretic separation in a 0.8% agarose gel, the YHR063c fragment about 1.2 kb in size was cut out of this and the DNA was isolated with the QuaexII Gel Extraction Kit (Qiagen, Hilden, Germany). It was then ligated into the plasmid pKK223-3, which had been opened with EcoRI and PstI, with T4 DNA ligase (Roche, Mannheim, Germany). The ligation batch was transformed into the *E. coli* strain XL1-Blue (Stratagene, LaJolla, Calif., USA). Tranformants were obtained by selection on LB meduim comprising 150 µg/ml ampicillin (Sigma Deisenhofen, Germany). Plasmid DNA from the ampicillin-resistant clones was prepared by alkaline lysis (Sambrook et al.: Molecular Cloning, A Laboratory Manual, Cold Spring Harbor Laboratory Press, 1989). Successful cloning was checked by restriction with EcoRI and PstI and subsequent separation in 0.8% agarose gel. The plasmid with the desired structure was given the name pKK-YHR063c.

EXAMPLE 15:

Complementation of the *E. coli* mutant FE5

To analyse the panE function of the YHR063c reading frame from *S. cerevisiae*, it was investigated whether expression of this reading frame can complement the need for pantothenic acid of the E, coli strain FE5 (example 1). This strain is mutated in the gene loci panE and ilvC. For this, the strain FE5 was first transformed with plasmid pKK-YHR063c.

The growth of the strain FE5/pKK-YRH063c on M9 minimal agar (Sambrook et al.: Molecular Cloning, A Laboratory Manual, Cold Spring Harbor Laboratory Press, 1989), which had been supplemented with 50 μg/ml ketoisovalerate (Kiv) and 50 μg/ml isoleucine (Ile), was then investigated as a function of the addition of pantothenate (50 μg/ml). The strain FE5/pKK223-3 served as a negative control and the strain FE4/pFE65 (example 4) as a positive control. Table 7 shows the result of the experiment: The S. cerevisiae reading frame YHR063c contained in plasmid pKK-YHR063c complements panE-ilvC double mutation of the E. coli strain FE5. The reading frame YRH063c has the function of a panE gene.

TABLE 7

| Strain | M9 + Kiv + Ile with pantothenate | M9 + Kiv + Ile without pantothenate |
| --- | --- | --- |
| FE5/pFE65 | growth | growth |
| FE5/pKK223-3 | growth | no growth |
| FE5/pKK-YHR063c | growth | growth |

EXAMPLE 16

Determination of the ketopantoate reductase Activity in Various Strains of Saccharomyces cerevisiae The S. cerevisiae strain JD242 (see example 14) was transformed with the plasmids pJDCEX2 and pJD-YHR063c by the method of Dohmen et al. (Dohmen et al., Yeast 7, 691(1991)). Selection for transformants was carried out on leucine-free minimal medium with 1.8% agar (see Tables 8a,b).

The nutrient medium used was a pantothenic acid-free variant of the Yeast Nitrogen Base-Minimal medium (YNB) described in the Difco manual (Michigan, USA;, $10^{th}$ edition, 1100–1102 (1084)). It additionally comprised glucose (2%), uracil (40 μg/ml), $CuSO_4$ (150 μM) for induction of the $P_{cup1}$ promoter of pJDCEX2 and pJD-YHR-063c, -Leu Drop-Out Supplement from CLONTECH (Heidelberg, Germany, Cat. no. 8605-1) (650 μg/ml) and the supplements ketopantoate (100 μg/ml) and β-alanine (100 μg/ml). The composition of the medium used is shown in Table 8a and b.

TABLE 8a

| Compound | Amount per liter |
| --- | --- |
| $(NH_4)_2SO_2$ | 5 g |
| $KH_2PO_4$ | 1 g |
| $MgSO_4*7H_2O$ | 0.5 g |
| NaCl | 0.1 g |
| $CaCl_2$ | 0.1 g |
| $H_3BO_3$ | 500 μg |
| $CuSO_4$ | 40 μg |
| KI | 100 μg |
| $FeCl_3*6H_2O$ | 200 μg |
| $MnSO_4*H_2O$ | 400 μg |
| $Na_2MoO_4*2H_2O$ | 400 μg |
| $ZnSO_4*7H_2O$ | 200 μg |
| Biotin | 2 μg |

TABLE 8a-continued

| Compound | Amount per liter |
| --- | --- |
| Folic acid | 2 μg |
| Inositol | 2 mg |
| Niacin | 400 μg |
| p-Aminobenzoic acid | 200 μg |
| Pyridoxine hydrochloride | 400 μg |
| Riboflavin | 200 μg |
| Thiamine hydrochloride | 400 μg |

TABLE 8b

| Additives | Amount per liter |
| --- | --- |
| Glucose | 20 g |
| Uracil | 40 mg |
| $CuSO_4$ | 24 mg |
| -Leu DO Supplement | 650 mg |
| Ketopantoate | 100 mg |
| β-Alanine | 100 mg |

250 ml conical flasks were filled with 50 ml of the stated nutrient medium, and the batch was inoculated with an individual colony from an agar plate with the aid of an inoculating loop (see Tables 8a,b) and incubated at 30° C. and 175 rpm for 72 hours. With this preculture, 50 ml of the same nutrient medium in a 250 ml conical flask were inoculated with the preculture such that the optical density (580 nm) was 0.5. After an incubation time of 24 hours at 30° C. and 175 rpm, the optical density was measured with a Novaspec II photometer from Pharmacia (Freiburg, Germany) at a measurement wavelength of 580 nm. It was 4.0 for both cultures. The specific ketopantoate reductase activity of the S. cerevisiae strains JD242/pJDCEX2 and JD242/pJD-YHR063c was determined by the method described by Shimizu et al. (Journal of Biological Chemistry 263:12077–12084 (1988)).

For this, cell extracts of the individual strains were obtained by means of a Hybaid RiboLyser (Heidelberg, Germany) and the RiboLyser Kit Red. The ketopantoate reductase activity of the extracts was determined with the aid of the NADPH consumption on addition of ketopantoate. The protein content was determined by the method of Bradfort (Bradfort, Analytical Biochemistry 72, 248ff. (1976)). A specific ketopantoate reductase activity of 3 mU/mg protein was determined for the control strain JD242/ pJDCEX2 and a specific activity of 386 mU/mg protein was determined for the strain JD242/pJD-YHR063c.

EXAMPLE 17

Formation of Pantothenate by Various Strains of Saccharomyces cerevisiae

The formation of pantothenate by the strains S. cerevisiae JD242/pJDDCEX2 and JD242/pJD-YHR063c was investigated in a batch culture.

250 ml conical flasks were filled with 50 ml of the nutrient medium stated in Tables 8a,b, and the batch was inoculated with an individual colony from an agar plate with the aid of an inoculating loop (see Table 8a,b) and incubated at 30° C. and 175rpm for 72 hours. With this preculture, 50 ml of the same nutrient medium in a 250 ml conical flask were inoculated with the preculture such that the optical density (580 nm) was 0.5. After an incubation time of 24 hours at 30° C. and 175rpm, the optical density (580 nm) and the pantothenate concentration were determined. For determination of the cell density, the optical density was measured with a Novaspec II photometer from Pharmacia (Freiburg, Germany) at a measurement wavelength of 580 nm. The pantothenate content was determined in the sterile-filtered culture supernatant.

The pantothenate (as the calcium salt) was determined with the aid of the strain *Lactobacillus plantarum* ATCC® 8014 as described in the handbook "DIFCO MANUAL" from DIFCO (Michigan, USA;, 10$^{th}$ Edition, 1100–1102 (1984)). The result is summarized in Table 9.

TABLE 9

| S. cerevisiae strain | Concentration [µg/ml] | Cell density [OD$_{580}$] | Productivity [µg/ml/OD$_{580}$] |
|---|---|---|---|
| JD242/pJDCEX2 | 0.93 | 4.0 | 0.023 |
| JD242/pJD-YHR063c | 1.12 | 4.1 | 0.027 |

References and patents cited herein are hereby incorporated by reference.

What is claimed is:

1. *E. coli* K12 strain FE6, which carries a valine resistance marker, deposited under the designation DSM 12379.

2. *E. coli* K12 strain FE7, deposited under the designation DSM 12380.

* * * * *